(12) United States Patent
Turchi et al.

(10) Patent No.: US 9,757,350 B2
(45) Date of Patent: Sep. 12, 2017

(54) SMALL MOLECULE INHIBITORS OF REPLICATION PROTEIN A THAT ALSO ACT SYNERGISTICALLY WITH CISPLATIN

(71) Applicants: Indiana University Research and Technology Corp., Indianapolis, IN (US); Indiana State University, Terre Haute, IN (US)

(72) Inventors: John J. Turchi, Indianapolis, IN (US); Richard Fitch, Terre Haute, IN (US)

(73) Assignees: Indiana University Research and Technology Corporation, Indianapolis, IN (US); Indiana State University, Terre Haute, IN (US)

( * ) Notice: Subject to any disclaimer, the term of this patent is extended or adjusted under 35 U.S.C. 154(b) by 0 days.

(21) Appl. No.: 14/598,380

(22) Filed: Jan. 16, 2015

(65) Prior Publication Data

US 2015/0231104 A1    Aug. 20, 2015

Related U.S. Application Data

(63) Continuation of application No. 13/824,318, filed as application No. PCT/US2011/052211 on Sep. 19, 2011, now Pat. No. 8,980,955.

(60) Provisional application No. 61/383,954, filed on Sep. 17, 2010, provisional application No. 61/387,784, filed on Sep. 29, 2010.

(51) Int. Cl.
*A61K 31/22* (2006.01)
*A61K 33/24* (2006.01)

(52) U.S. Cl.
CPC .............. *A61K 31/22* (2013.01); *A61K 33/24* (2013.01)

(58) Field of Classification Search
None
See application file for complete search history.

(56) References Cited

PUBLICATIONS

Gura et. al. (Science, 1997, 278:1041-1042).*
Johnson et. al. (British Journal of Cancer, 2001, 84:1424-1431).*
(Continued)

*Primary Examiner* — Marcos Sznaidman
*Assistant Examiner* — Rayna B Rodriguez
(74) *Attorney, Agent, or Firm* — Barnes & Thornburg LLP

(57) ABSTRACT

Replication protein A (RPA) is a single-strand DNA-binding protein with essential roles in DNA replication, recombination and repair. Small molecule inhibitors (SMIs) with the ability to disrupt RPA binding activity to ssDNA have been identified and assessed using both lung and ovarian cancer cell lines. Lung cancer cell lines demonstrated increased apoptotic cell death following treatment with the SMI MCI13E, with IC50 values of ~5 μM. The A2780 ovarian cancer cell line and the p53-null lung cancer cell line HI 299 were particularly sensitive to MCI13E treatment with $IC_{50}$ values below 3 μM. Sequential treatment with MCI13E and cisplatin resulted in synergism, suggesting that decreasing RPA's DNA binding activity via a SMI may disrupt RPA's role in cell cycle regulation. Thus, RPA SMIs hold the potential to be used as single agent chemotherapeutics or in combination with current chemotherapeutic regimens to increase their efficacy.

9 Claims, 35 Drawing Sheets

(56) References Cited

PUBLICATIONS

Shuck et al., Targeted inhibition of replication protein A reveals cytotoxic activity, synergy with chemotherapeutic DNA-damaging agents, and insight into cellular function. Cancer Res. Apr. 14, 2010, vol. 70, No. 8, p. 3189-3198, p. 3189, col. 2, para 1, p. 3191, col. 1, para 1, p. 3192, Table 1, p. 3193, col. 1, para 1, Fig. 2D, p. 3194, Fig 3, p. 3196, col. 1, para 2.
Bernhardt et al., Terpene conjugates of diaminedichloridoplatinum (II) complexes: antiproliferative effects in HL-60 leukemia, 518A2 melanoma, and HT-29 colon cancer cells. Chemistry & Biodiversity, Aug. 2008, vol. 5, No. 8, p. 1645-1659. abstract, p. 1645, para 1, p. 1647, Scheme 1, p. 1649, Table 1.
Turchi et al. ("Targeting Nucleotide Excision Repair as a Mechanism to Increase Cisplatin Efficacy." Platinum and Other Heavy Metal Compounds in Cancer Chemotherapy: Molecular Mechanisms and Clinical Applications. Humana Press, Jan. 9, 2009, p. 177-187).
Theobald, D. L., et al., "Nucleic Acid Recognition by Ob-Fold Proteins," Annu. Rev. Biophys. Biomol. Struct., 2003, 32, 115-133.
Wang, F., et al., "The POT1-TPP1 telomere complex is a telomerase processivity factor," Nature, 2007, 445, 506-510.
Murzin, A. G., "Ob(oligonucleotide/oligosaccharide binding}-fold: common structural and functional solution for nonhomologous sequences," EMBO J., 1993,12, 861-867.
Bochkareva, E., et al., "Structure of the RPA trimerization core and its role in the multistep DNA-binding mechanism of RPA," EMBO J., 2002, 21, 1855-1863.
Pfuetzner, R. A., et al., "Replication Protein A Characterization and Crystallization of the DNA Binding Domain," J. Biol. Chem., 1997, 272, 430-434.
Umezu, K., et al., "Genetic analysis of yeast RPA1 reveals its multiple functions in DNA metabolism," Genetics, 1998, 148, 989-1005.
Haring, S. J., et al., "Cellular Functions of Human RPA1 Multiple Roles of Domains in Replication, Repair, and Checkpoints," J. Biol. Chem., 2008, 283, 19095-19111.
Zamble, D. B. et al., "Repair of Cisplatin-Dna Adducts by the Mammalian Excision Nuclease," Biochemistry, 1996, 35, 10004-10013.
Patrick, S. M., et al., "Replication Protein A (RPA) Binding to Duplex Cisplatin-damaged DNA Is Mediated through the Generation of Single-stranded DNA," J. Biol. Chem., 1999, 274, 14972-14978.
Stauffer, M. E., et al., "Physical Interaction between Replication Protein a and Rad51 Promotes Exchange on Single-stranded DNA,"J. Biol. Chem., 2004, 279, 25638-25645.
Soustelle, C., et al., "Replication Protein A Is Required for Meiotic Recombination in Saccharomyces cerevisiae," Genetics, 2002, 161, 535-547.
Andrews, B. J., et al., "Kinetic Analysis of the Ku-DNA Binding Activity Reveals a Redox-dependent Alteration in Protein Structure That Stimulates Dissociation of the Ku-DNA Complex," J. Biol. Chem., 2006, 281, 13596-13603.
Andrews, B. J. et al., "Development of a high-throughput screen for inhibitors of replication protein a and its role in iucleotide excision repair," Mol. Cancer Ther., 2004, 3, 385-391.
Bochkareva, E., et al., "Structure of the major single-stranded DNA-binding domain of replication protein a suggests a dynamic mechanism for DNA binding," EMBO J., 2001, 20, 612-618.
Moellering, R. E., et al., "Direct inhibition of the NOTCH transcription factor complex," Nature, 2009, 462, 182-188.
Saha, M. N., et al., "MDM2 antagonist nutlin plus proteasome inhibitor velcade combination displays a synergistic anti-myeloma activity," Cancer Biol. Ther., 2010, 9,:11, 936-944.
Anciano Granadillo, V. J., et al., "Targeting the Ob-Folds of Replication Protein a with Small Molecules," J. Nucleic Acids, 2010, 304035, 11 pages.
Einhom, L. H., "Curing metastatic testicular cancer," Proceedings of the National Academy of Sciences of the United States of America, 2002, 99, 4592-4595.
Wakasugi, M., et al., "Order of Assembly of Human DNA Repair Excision Nuclease," J. Biol. Chem., 1999, 274, 18759-18768.
Wood, R. D., "Nucleotide Excision Repair in Mammalian Cells," J. Biol. Chem., 1997, 272, 23465-23468.
Cimprich, K. A. et al., "ATR: an essential regulator of genome integrity," Nat. Rev. Mol. Cell Biol., 2008, 9, 616-627.
Boeckman, H. J., et al., "Cisplatin sensitizes cancer cells to ionizing radiation via inhibition of non-homologous end joining," Mol. Cancer Res., 2005, 3, 277-285.
Waga, S., et al., "The DNA Replication Fork in Eukaryotic Cells," Annu. Rev. Biochem., 1998, 67, 721-751.
Raghunathan, S., et al., "Structure of the DNA binding domain of E. coli SSB bound to ssDNA," Nat. Struct. Biol., 2000, 7, 648-652.
Wold, M. S., "Replication Protein A:A Heterotrimeric, Single-Stranded DNA-Binding Protein Required for Eukaryotic DNA Metabolism," Annual Review of Biochemistry, 1997, 66, 61-92.
Bochkarev, A. et al., "From RPA to BRCA2: lessons from single-stranded Dna binding by the OB-fold," Current Opinion in Structural Biology, 2004, 14, 36-42.
Lei, M., et al., "Structure of human POT1 bound to telomeric single-stranded DNA provides a model for chromosome and-protection," Nat. Struct. Mol. Biol., 2004, 11, 1223-1229.
Yang, H., et al., "BRCA2 function in Dna binding and recombination from a BRCA2-DSS1-ssDNA structure," Science, 2002, 297, 1837-1848.
De Vlaminck, I., et al., "Torsional regulation of hRPA-induced unwinding of double-stranded DNA," Nucleic Acids Res., 2010, 38, 4133-4142.
Patrick, S. M., et al., "Xeroderma Pigmentosum Complementation Group a Protein (XPA) Modulates RPA-DNA Interactions via Enhanced Complex Stability and Inhibition of Strand Separation Activity," J. Biol. Chem., 2002, 277, 16096-16101.
Ng, P. Y. et al., "Synthesis of diverse lactam carboxamides leading to the discovery of a new transcription-factor inhibitor," Angew. Chem. Int. Ed Engl., 2007, 46, 5352-5355.
Patrick, S. M., et al., "Recognition of Cisplatin-DNA Interstrand Cross-Links by Replication Protein A," Biochemistry, 2008, 47, 10188-10196.
Reed, E., "Platinum-DNA adduct, nucleotide excision repair and platinum based anti-cancer chemotherapy," Cancer Treat. Rev., 1998, 24, 331-344.
Wyka, I. M., et al., "Replication Protein a Interactions With DNA: Differential Binding of the Core Domains and Analysis of the DNA Interaction Surface," Biochemistry, 2003, 42, 12909-12918.
Bochkarev, A., et al., "Structure of the single-stranded-Dna-binding domain of replication protein a bound to DNA," Mature, 1997, 385, 176-181.
Lei, M., et al., "DNA self-recognition in the structure of Poll bound to telomeric single-stranded DNA," Nature, 2003, 126, 198-203.
Croy, J. E., et al., "A new model for Schizosaccharomyces pombe telomere recognition: the telomeric single-stranded DNA-binding activity of Pot11-389," J. Mol. Biol., 2006, 361, 80-93.
Neher, T. M., et al., "Novel Irreversible Small Molecule Inhibitors of Replication Protein A Display Single Agent Activity and Synergize with Cisplatin," 2011, Mol. Cancer Ther., 10, 1796-1806.
Chou, T. C., et al., "Quantitative analysis of dose-effect relationships: the combined effects of multiple drugs or enzyme inhibitors," Advances in Enzyme Regulation, 1984, 22, 27-55.
Zou, L. et al., "Sensing DNA damage through Atrip recognition of RPA-ssDNA complexes," Science, 2003, 300, 1542-1548.

* cited by examiner

US 9,757,350 B2

SMALL MOLECULE INHIBITORS OF REPLICATION PROTEIN A THAT ALSO ACT SYNERGISTICALLY WITH CISPLATIN

PRIORITY CLAIM

This application is a Continuation Application of U.S. application Ser. No. 13/824,318, filed on Oct. 3, 2013, which itself is a U.S. National Phase Patent Application based on International Application Serial No. PCT/US2011/052211 filed Sep. 19, 2011, which claims the benefit of U.S. provisional patent applications No. 61/383,954 filed on Sep. 17, 2010 and 61/387,784 filed on Sep. 29, 2010, the disclosures of which are incorporated herein by reference in their entirety.

STATEMENT OF GOVERNMENT RIGHTS

This invention was made with government support under grant number CA082741 awarded by The National Institute of Health. The government has certain rights in the invention.

FIELD OF THE INVENTION

This invention relates generally small molecule inhibitors of inhibit Replication Protein A (RPA) including mildly reactive halo-esters of isoborneol.

BACKGROUND

The nucleotide excision repair pathway (NER) is a highly versatile DNA repair pathway present in a number of organisms from bacteria to mammals which requires the contribution of over thirty proteins. The NER pathway repairs a wide array of bulky DNA damage from a variety of sources such as, reactive chemicals and exposure to UV light. Numerous non-enzymatic protein-DNA interactions are essential for the proper functioning of the NER machinery and play important roles in nearly every reaction in the pathway including lesion recognition. Damaged DNA is recognized by the trimeric complex consisting of Xeroderma Pigmentosum Group C (XPC), Rad23B and Centrin 2 during global genomic nucleotide excision repair (GG-NER) while the stalling of RNA polymerase during transcription is the method of damage recognition during transcription-coupled (TC) NER. Following damage recognition the pre-incision NER complex is completed with the subsequent recruitment of Xeroderma Pigmentosum Group A (XPA) protein, Transcription Factor II H (TFIIH) protein and the human single-stranded DNA (ssDNA) binding protein, Replication protein A (RPA) to the site of DNA damage. RPA is one of the first proteins that functions in both the GG and TC-NER subpathways. RPA is a heterotrimeric DNA binding protein containing three subunits p70, p34, and p14 (kDa) and plays an important role in DNA replication and recombination in addition to repair. The p70 RPA subunit contains DNA binding domains A and B (DBD-A and DBD-B) and contributes most significantly to the RPA-ssDNA interaction. The RPA p34 subunit also contains an OB-fold and interacts with additional proteins including XPA while the 14 kDA subunit plays a role in protein stability. The RPA-DNA interaction is essential for the formation of the NER preincision complex and proper functioning of the NER pathway. Disruption of this essential protein-DNA interaction via small molecule inhibitors (SMIs) should reduce the NER efficiency. Previous reports have demonstrated that decreased expression levels of essential NER proteins, such as XPA result in decreased NER capacity and removal of cisplatin adducts. Furthermore, increased expression of ERCC1-XPF was demonstrated to correlate with cisplatin resistance in ovarian cancer cell lines. Taken together, these data suggest that expression level of essential NER proteins affects the efficiency of the NER machinery. Using SMIs to inhibit RPA-DNA interactions and consequently the function of the NER machinery may increase the efficacy of DNA-damaging chemotherapeutics, particularly in tissues where enhanced repair via NER is a resistance mechanism.

The importance of RPA in DNA replication has been demonstrated by genetic studies in yeast, genetic knockdown studies in human cells and more recently in chemical genomic studies with a small molecule inhibitor of RPA. RPA plays multiple roles in DNA replication including assembly of pre-replication complexes and stabilization of ssDNA following helicase-catalyzed unwinding. Moreover, very recent data demonstrating that RPA can unwind duplex DNA has led to a model where RPA may help in maintaining double stranded DNA stability throughout replication. Inhibition of any one of these steps is likely to have deleterious effects on DNA replication and ultimately cell viability.

RPA inhibition with a recently identified SMI of RPA, TDRL-505, has been demonstrated to synergize with cis-platin in a human lung cancer cell model (1). This effect is likely to be a function of alterations in DNA repair, specifically nucleotide excision repair (NER), though effects on homologous recombination cannot be ruled out. Cisplatin, cis-diamminedichloroplatinum (II), is commonly used as a chemotherapeutic drug in cancer treatment that forms cytotoxic intra- and inter-strand DNA-cisplatin adducts. DNA-cisplatin adducts are repaired mainly through the NER pathway and RPA has been shown to preferentially bind to duplex cisplatin-damaged DNA compared to undamaged DNA through the development of ssDNA. RPA is also responsible for the recognition of inter-strand cross-links caused by cisplatin treatment. Cisplatin resistant cancers have been linked to enhanced DNA repair and thus the ability to impact DNA repair efficiency via modulation of RPA's DNA binding activity is of potential clinical use to treat cancer in conjunction with platinum agents. Etoposide, a common chemotherapeutic drug that induces replication fork stalling by inhibiting topoisomerase II, was also demonstrated to synergize with the RPA SMI TDRL-505 (1). This synergistic activity is predicted to increase the toxic effects exerted by etoposide both in the context of replication and DNA repair. RPA's role in homologous recombination may be mediating this effect where DNA double strand breaks are processed to generate a 3' ssDNA overhang to which RPA binds to help catalyze RAD51 dependent strand exchange. In *Saccharomyces cerevisiae*, mutations within the DNA binding domain and protein-protein interaction regions of ScRPA lead to highly decreased meiotic recombination. This is consistent with data obtained from SMIs of hRPA demonstrating decreased DNA replication, repair and recombination in cancer cells and increased efficacy of treatments with DNA damaging agents. Given, RPA's role in cancer cell drug resistance there is a need for materials and methods for regulating this enzymes activity in some cells, some embodiments of the invention disclosed herein address this need.

SUMMARY

Some embodiments include methods of inhibiting Replication Protein A (RPA), comprising the steps of: providing at least one tricyclic anhydride or terpene derivative; supplying at least one isoform of RPA; and contacting said tricyclic anhydride or a terpene derivative with the RPA. In some embodiments the inhibitor of RPA is selected from the group consisting of MCI13E and MCI13F. In some embodiments RPA is contacted with a halo-ester isoborneol in vitro. In still other embodiments RPA is contacted with the halo-ester isoborneol in vivo.

Still other embodiments include methods of affecting eukaryotic cell viability, comprising the steps of: providing at least one tricyclic anhydride or a terpene derivative; supplying at least one eukaryotic cell wherein the cell includes at least one isoform of RPA; and contacting said tricyclic anhydride or a terpene derivative with the RPA. In some embodiments the halo-ester isoborneol is selected from the group consisting of MCI13E and MCI13F. In some embodiments the eukaryotic cell is contacted with a halo-ester isoborneol in vitro. In still other embodiments the eukaryotic cell is contacted with the halo-ester isoborneol in vivo.

Some embodiments include method of treating cancer, comprising the steps of: providing at least one tricyclic anhydride or a terpene derivative; supplying at least one cancer cells, wherein the cancer cell expresses at least isoform of RPA; and contacting said tricyclic anhydride or a terpene derivative with the cancer cell. In some embodiments the halo-ester isoborneol is selected from the group consisting of MCI13E and MCI13F. In some embodiments cancer cell is contacted with a tricyclic anhydride or a terpene derivative that inhibits RPA in vitro. In still other embodiments cancer cell is contacted with a tricyclic anhydride or a terpene derivative that inhibits RPA in vivo. In some embodiment the cancer cell is in either a human or an animal.

Still other embodiments include, a halo-ester isoborneol, wherein the halogen is selected from the group consisting of fluorine, chlorine, bromine and iodine. In some embodiment the compound is selected from the group consisting of MCI13E and MCI13F.

Some embodiments of the invention include methods of inhibiting Replication Protein A, comprising the steps of contacting a tricyclic anhydride or a terpene derivative that inhibits RPA with a molecule of Replication Protein A, (RPA) wherein said borneol at least partially inhibits the activity of Replication Protein A. In some embodiments the compounds at least partially inhibit the RPA in vivo and/or in vitro. In some embodiments the terpene derivative is a halo-ester isoborneol substituted with at least one halogen selected from the group consisting of fluorine, chlorine, bromine and iodine. And in some embodiments the RPA inhibitor is TDLR-003, MCI13E, and MCI13F. In still other embodiments the RPA inhibit is the compound referred to herein as CheSS19. The contacting step between the compounds and RPA may in vitro and/or in vitro, it being understood that different compounds may be more or less amenable for use either in vitro or in vivo.

Still other embodiments of the invention include methods of affecting eukaryotic cell viability, comprising the steps of: contacting a tricyclic anhydride or a terpene derivative that inhibits RPA with a eukaryotic cell, wherein the cell is expressing or has the potential to express RPA. In some embodiments the eukaryotic cell contacted with the RPA inhibit is a cancer cell. Some methods of interfering with eukaryotic cell growth and or death further include the step of dosing the eukaryotic cell with at least one compound that damages DNA in vivo. In some embodiments the compound that damages DNA in vivo promotes the formation of intrastrand linkages between adjacent nucleotides; in some embodiments the compound that damages DNA is cisplatin (cis-diamminedichloroplatinum[III]). Treating cells with tricyclic anhydrides or terpene derivative inhibitors of RPA and compounds such as cisplatin may be accomplished either concurrently of sequentially. One particularly effective means of treating cancer cells is to first dose or otherwise contact the cell with chsplati or another compound that damages DNA and then contact the same set of cells with at least one tricyclic anhydride or a terpene derivative that inhibits RPA.

In some embodiments the terpene derivative that is used to control the growth and/or viability of cells such as cancer cells is halo-ester isoborneol substituted with at least one halogen selected from the group consisting of fluorine, chlorine, bromine and iodine. In some embodiments the halo-ester isoborneol used to treat the cell is selected from the group consisting of: TDLR003, MCI13E, and MCI13F. In still other embodiments the tricyclic anhydride used to treat the cell either alone or in combination with a compound that promotes damage to cellular DNA is CheSS19.

Still other embodiments of the invention include methods of treating cancer, comprising the steps of treating a patient with a therapeutically effective amount of at least one tricyclic anhydride or a terpene derivative or a pharmaceutically acceptable salt thereof, wherein said tricyclic anhydride or a terpene derivative at least partially inhibits the activity of Replication Protein A in vivo. In some embodiments the methods of treating cancer in a human or animal patient further includes the step of dosing a eukaryotic cell, particularly a cancer or pre-cancer cell, with a therapeutically effective amount of at least one compound that damages DNA in vivo. In some embodiments the compound that damages DNA in vivo may do so by promoting the formation of intrastrand linkages between adjacent nucleotides. In some embodiments the compound that damages DNA and is used in combination with at least one tricyclic anhydride or a terpene derivative inhibitor of RPA is cis-diamminedichloroplatinum[III], or a pharmaceutically acceptable salt thereof. In some embodiments the combination of the DNA damaging agent and the tricyclic anhydride or a terpene derivative RPA inhibitor is administered- to the cells or the human or animal patient either concurrently or sequentially. In some embodiments the patient or cells are first treated with a compound that damages DNA before they are treated or otherwise contacting with a tricyclic anhydride or a terpene derivative compound that inhibits RPA. In some embodiments the terpene derivative is a halo-ester isoborneol, or a pharmaceutically acceptable salt thereof and said halo-ester isoborneol is substituted with at least one halogen selected from the group consisting of fluorine, chlorine, bromine and iodine. In some embodiments the halo-ester isoborneol is selected from the group consisting of: TDLR003, MCI13E, and MCI13F.23. In some embodiments the tricyclic anhydride borneol used to treat the cell is CheSS19. 24.

In some embodiments the therapeutically effective amount of the tricyclic anhydride or a terpene derivative that inhibits RPA and is administered to the patient is on the order of about 400 mg to about 200 mg of pharmaceutically active compound per $kg^{-1}$ of patient body weight, or less. In other embodiments the therapeutically effective amount of the tricyclic anhydride or a terpene derivative is on the order of about 100 mg of pharmaceutically active compound per $kg^{-1}$ of patient body weight, or less. And in still other embodiments the therapeutically effective amount of the tricyclic anhydride or a terpene derivative is on the order of about 50 to about 10 mg of pharmaceutically active compound per kg$^{-1}$ of patient body weight.

Still other embodiments of the invention include methods for labelling Replication Protein A (RPA), comprising the steps of: contacting at least one molecule of Replication Protein A with at least one tricyclic anhydride or a terpene derivative, wherein said tricyclic anhydride or a terpene derivative includes a readily detectable moiety. In some embodiments the readily detectable moiety is selected from the group consisting of: a radio-isotope, a chemiluminescent group, a fluorophore or an antigen capable of immuno-detection. And in some embodiments the immuno-detection group includes biotin.

Some embodiments include a system for identifying RPA comprising at least one labelled borneol compound that binds to RPA. In some embodiments this system is used to diagnose other cells that have suffered damage to their DNA or that are sensitive to treatment with pharmaceutical compounds the treat cells by at least partially inhibiting the activity of RPA.

BRIEF DESCRIPTION OF THE SEQUENCES

SEQ. ID No. 1 5'-GGA GAC CGA AGA GGA AAA GAA GGA GAG AGG-3'. A synthetic oligonucleotide substrate of the 3Pc3 sequence.

SEQ. ID No. 2 5'-CTA GAA AGG GGG AAG AAA GGG AAG AGG CCA GAG A-3'. A 34-mer synthetic oligonucleotide substrate.

SEQ. ID No. 3 5'-GGT TAC GGT TAC CCC-3' A 15-mer synthetic oligonucleotide substrate.

BRIEF DESCRIPTION OF THE FIGURES

Referring now to FIG. 7A. Model of the ssDNA-binding interface of OB-fold containing proteins.

DESCRIPTION

Figure 1A:
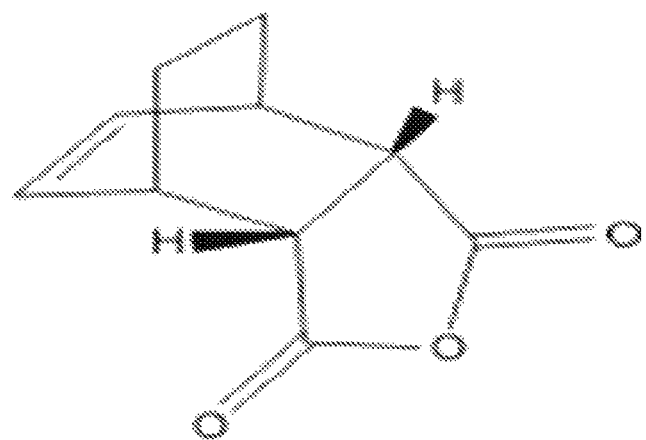
FIG. 1A. Structure of CheSS19.
Figure 1B:
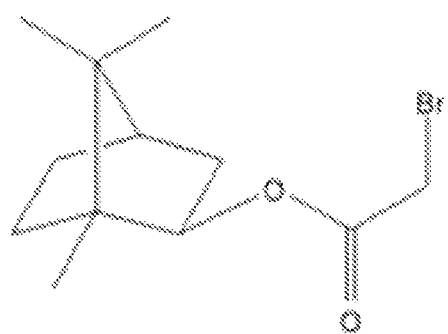
FIG. 1B. Structure of MCI13E.
Figure 1C:
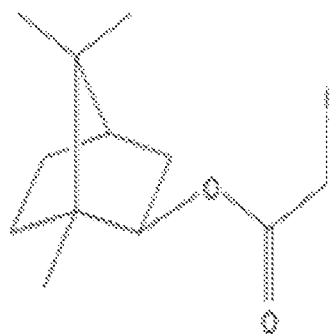
FIG. 1C. Structure of MCI13F.
Figure 1D:
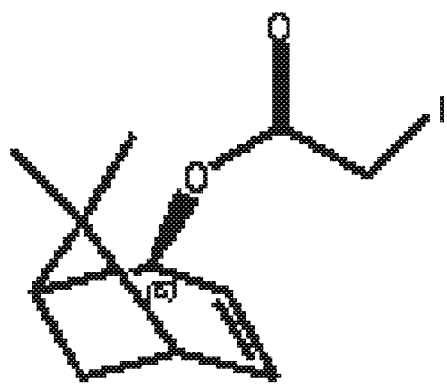
FIG. 1D. Structure of MCI17E.
Figure 1E:
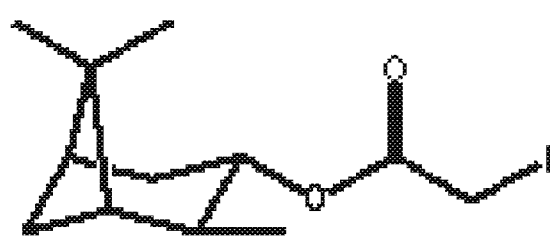
FIG. 1E. Structure of MCI17F.
Figure 1F:
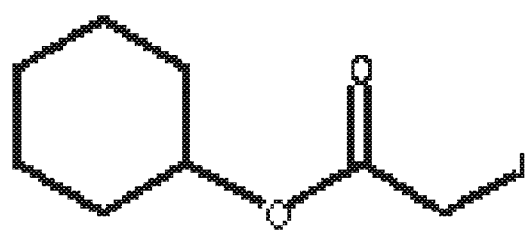
FIG. 1F. Structure of MCI19.
Figure 1G:
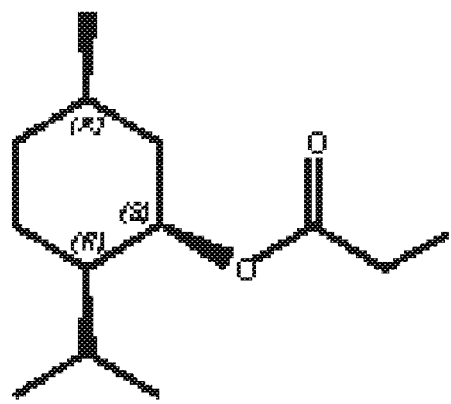
FIG. 1G. Structure of MCI1ID.
Figure 1H:
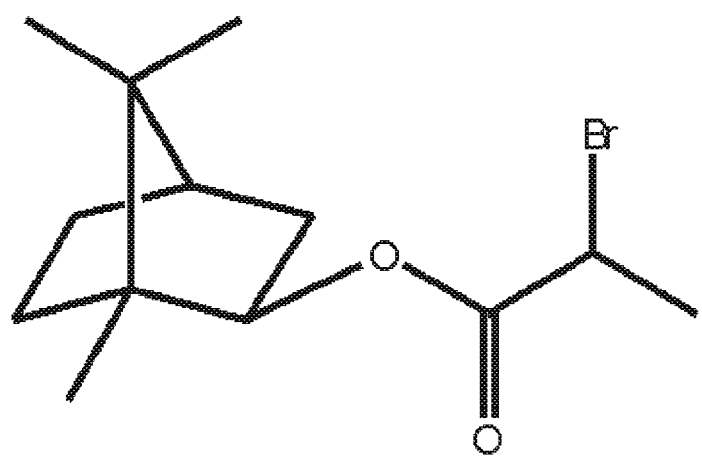
FIG. 1H. Structure of TDRL-003.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of the invention.

As used herein the phrase 'tricyclic anhydrides or a terpene derivatives' includes all of the compounds disclosed in FIGS. 1A-1J and all variations thereof.

As used herein, unless explicitly stated otherwise or clearly implied otherwise the term 'about' refers to a range of values plus or minus 10 percent, e.g. about 1.0 encompasses values from 0.9 to 1.1

As used herein, unless explicitly stated otherwise or clearly implied otherwise the terms 'therapeutically effective dose,' 'therapeutically effective amounts,' and the like, refers to a portion of a compound that has a net positive effect on the health and well being of a human or other animal. Therapeutic effects may include an improvement in longevity, quality of life and the like these effects also may also include a reduced susceptibility to developing disease or deteriorating health or well being. The effects may be immediate realized after a single dose and/or treatment or they may be cumulative realized after a series of doses and/or treatments.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For addition information on some pharmaceutically acceptable salts that can be used to practice the invention please reviews such as Berge, et al., 66 J. PHARM. SCI. 1-19 (1977), Haynes, et al, J. Pharma. Sci., Vol. 94, No. 10, October 2005, pgs. 2111-2120 and the like.

Replication protein A (RPA) is an essential protein involved in numerous DNA metabolic pathways including DNA replication, repair and recombination. RPA's activity in these pathways is, in part, a function of its single-stranded DNA (ssDNA) binding activity. RPA is a heterotrimeric protein comprised of 70-, 34- and 14-kDa subunits (4) and binds to DNA through interactions with a series of oligonucleotide/oligosaccharide binding (OB-folds) that display a high affinity for ssDNA (5). OB-folds are found in numerous proteins, specifically those that perform their function through the interaction with single-stranded nucleic acid structures including tRNA synthetases, telomeres, and replication and repair intermediates (6). The human telomeric DNA binding proteins, POT 1 and TPP 1 both use OB-folds to recognize and bind the 3' ssDNA overhang of telomeres. The breast cancer susceptibility protein, BRCA2, has three OB-folds that confer binding to ssDNA, which stimulates RAD51 mediated recombination. The OB-fold, also referred to as a Greek key motif, consists of two three-stranded anti-parallel β-sheets in which one strand is shared between them, forming a β-barrel structure. An α-helix is typically located between strands 3 and 4, which packs against the bottom of the β-barrel. The RPA 70-kDa subunit contains four putative OB-folds, two of which (A and B) comprise the central DNA binding domain (DBD-A/B), which, contributes the majority of the ssDNA binding activity of the heterotrimeric protein. While other DNA binding domains within RPA include zinc ribbons and helix-turn-helix motifs (7), the OB-fold of DBD-A/B possess aromatic amino acid residues (F238 and F269 in DBD-A and W361 and F386 in DBD-B) that provide critical base-stacking interactions. A recombinant construct containing the DBD-A/B of RPA has been expressed, purified, and shown to be sufficient to bind DNA.

In order to investigate the mechanisms of small molecule inhibition of RPA, the in vitro activity of a series of terpenes and their interactions with various RPA constructs were analyzed. The binding and interaction with full-length heterotrimeric RPA and a construct comprised of just DBD-A/B were assessed. The data presented herein suggest different modes of binding and interactions between the various classes of compounds and RPA, suggesting that they potentially target different OB-folds or different regions of the protein structure. Data demonstrating that the various SMIs are specific for the RPA protein-DNA interaction and do not inhibit the interaction between ssDNA and other OB-fold containing proteins is also presented.

CheSS19 Inhibits Both WT RPA and RPA AB Region Interactions with DNA.

The bicyclic-isoborneol class of RPA SMI's was initially identified as a pharmacophore in a screen of the NCI diversity set and analogs identified in a subsequent screen of the NCI developmental therapeutics general library (8). Initial SAR analysis indicated variation in the bridging structure had minimal effects on RPA inhibitory activity while creating reactive anhydrides greatly increased activity (9). To ascertain if the tricylic anhydride, CheSS19 (FIG. 1A), also inhibited DNA binding via an interaction with the central DBD-A/B, its inhibitory activity towards the DBD-A/B construct and full-length heterotrimeric RPA was determined using EMSA analysis.

Figure 3A:
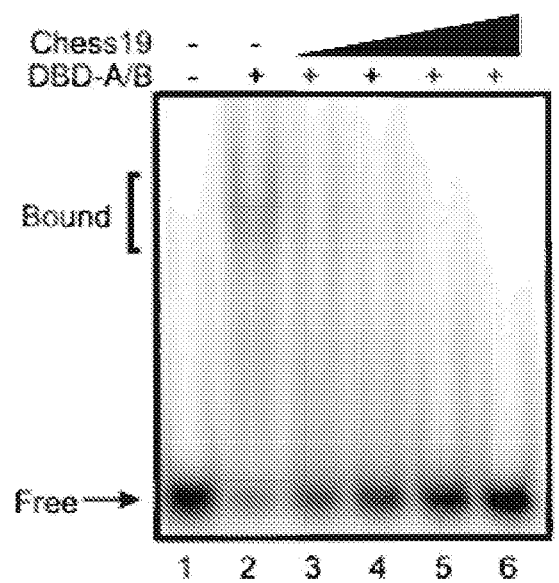
FIG. 3A. EMSA blot illustrating CheSS19 inhibition of RPA.
Figure 3B:
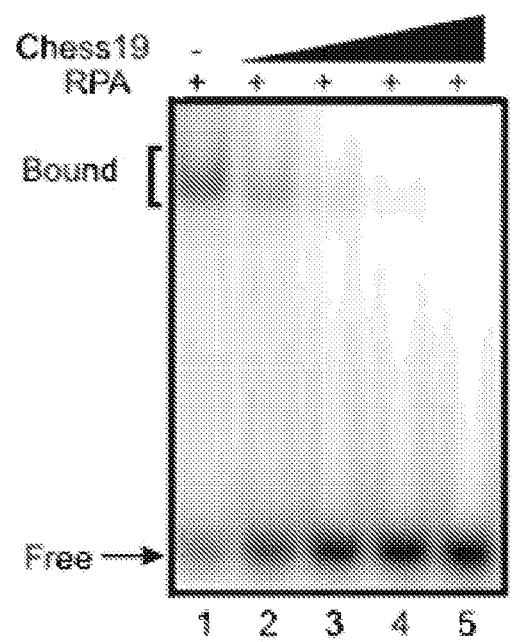
FIG. 3B. EMSA blot illustrating CheSS19 inhibition of full-length heterotrimeric RPA as assessed by EMSA.
Figure 3C:
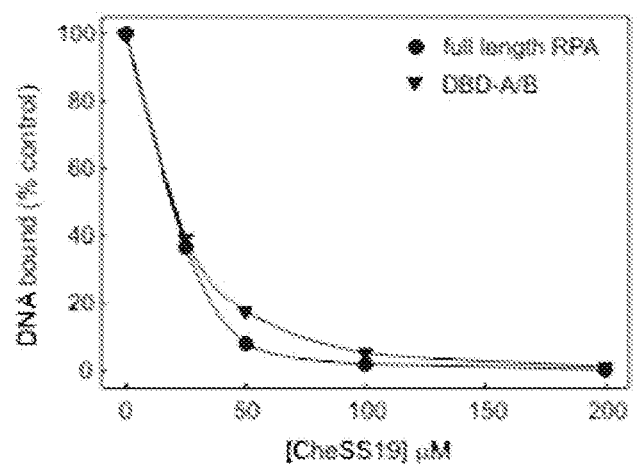
FIG. 3C. Quantification of the binding data presented in FIGS. 3A and 3B.

Referring now to FIG. 3A. EMSA blot illustrating CheSS19 inhibition of RPA. Irreversible inhibition of RPA DBD-A/B-DNA binding activity by CheSS19. A, EMSA analysis of CheSS19 inhibition of RPA DBD-A/B. Reactions contained 12.5 mM DNA, 50 nM DBD-A/B and 0, 25, 50 100 and 200 µM CheSS19 (Lanes, 2-6, respectively). Referring now to FIG. 3B. EMSA blot illustrating CheSS19 inhibition of full-length heterotrimeric RPA as assessed by EMSA. Reactions were identical to those in FIG. 3A except contained 25 nM full-length RPA. Referring now to FIG. 3C. Quantification of the binding data presented in FIGS. 3A and 3B. The results demonstrate that CheSS19 inhibits the DNA binding activity of the DBD-A/B construct with similar potency to the heterotrimeric RPA preparation (FIGS. 3A-C).

Irreversible Inhibition of RPA by CheSS19

Figure 3D:
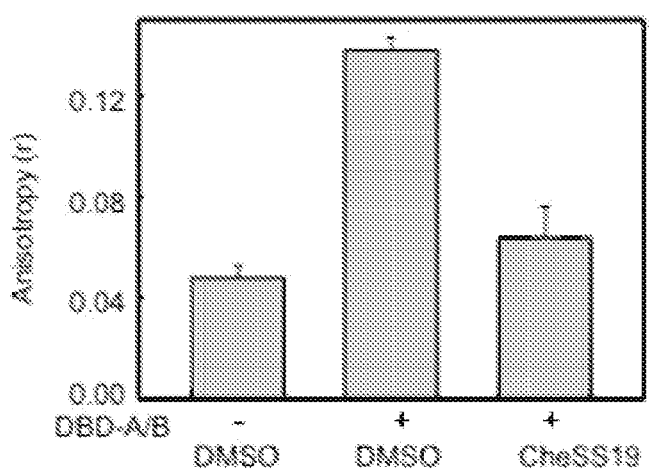
FIG. 3D. Bar graph showing results of fluorescence polarization analysis of CheSS19 inactivated RPA DBD-A/B.

It was demonstrated previously that CheSS19 inhibition of full-length RPA was irreversible (9), the reversibility of the inhibition of DBD-A/B binding to DNA was assessed. In an experiment reported herein, DBD-A/B was incubated with CheSS19 and then the reaction mix dialyzed overnight to remove dissociable inhibitor. Following dialysis, the protein was assessed for binding in a fluorescence polarization assay and the data demonstrate that following dialysis, CheSS19 was able to inhibit DBD-A/B DNA binding activity compared to protein incubated with DMSO vehicle (FIG. 3D). These results are consistent with CheSS19 inhibiting DBD-A/B in an irreversible manner. Referring now to FIG. 3D. Bar graph showing results of fluorescence polarization analysis of CheSS19 inactivated RPA DBD-A/B. Referring now to FIG. 3D, RPA DBD-A/B was pre-incubated with vehicle (1% DMSO) or CheSS19 (1 pmol in 1% DMSO) for 30 minutes at 37° C. Following incubation, the reaction mix was dialyzed versus H1 buffer overnight at 4° C. The protein was recovered and DNA binding activity measured by FP analysis of binding to an F-dT12 substrate was performed as described in "Methods". Bar 1, DNA control, Bar 2, control vehicle treated DBD-A/B, Bar 3, Chess19 treated DBD-A/B. The data represent the mean and range of two independent experiments.

Figure 4A:
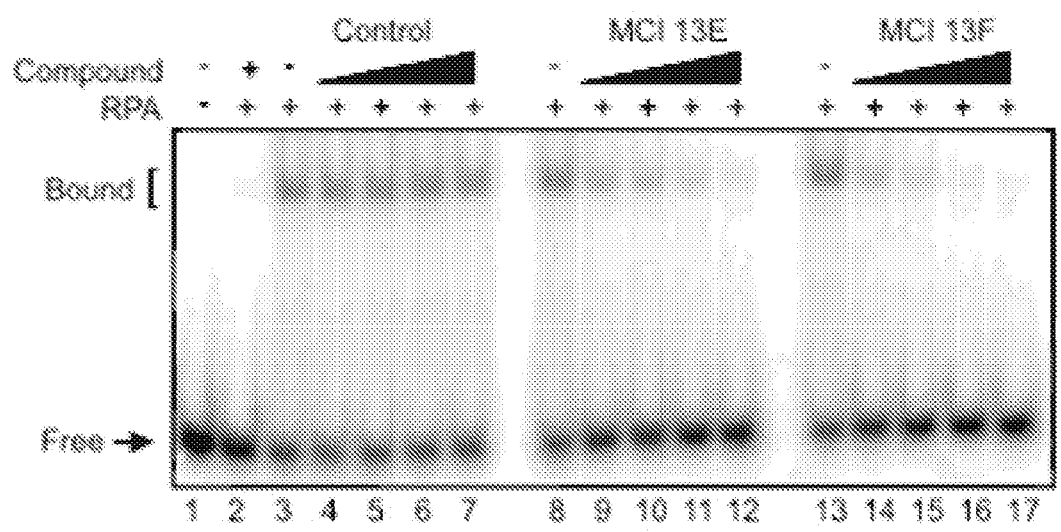
FIG. 4A. Gel showing effect of small molecule on RPA.
Figure 4B:
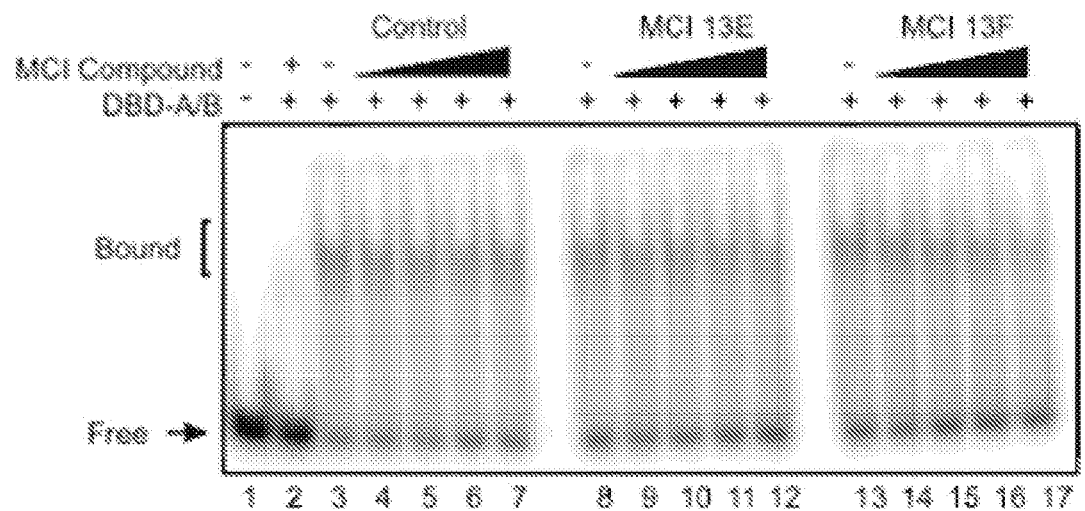
FIG. 4B. Gel showing effect of bicyclic isoborneol halo-esters on DBD-A/B labeled poly substrate.

While the anhydride groups in the active CheSS series are effective at inhibiting RPA in vitro, no cellular activity was observed following treatment with this series of compounds (data not shown). This inactivity is potentially a result of the highly reactive anhydride reacting non-specifically with other components or hydrolyzing to an unreactive di-carboxylic acid prior to encountering RPA in the cell nucleus. Next a less reactive substituent was employed to assess in vitro inhibition and analyzed a series of halo-ester derivatives of isoborneol. Synthesis and analysis with the bromo- and iodo-esters MCI13E and F, respectively (FIGS. 1B and C) revealed inhibition of the full-length heterotrimer RPA in EMSA analysis with the iodo-containing compound (MCI13F) being slightly more effective (FIG. 4A). Referring now to FIG. 4A Inhibition of full-length heterotrimeric RPA but not DBD-A/B-DNA binding activity by the MCI13 series of bicyclic isoborneol halo-esters. Increasing concentration of control compound, MCI13E or MCI13F were titrated in DNA binding reactions containing full-length heterotrimeric RPA. Binding to [$^{32}$P]-ss 30-base 3pC3 DNA was assessed by EMSA as described in "Methods". Referring now to FIG. 4B. The same inhibitor concentrations were assessed in reactions measuring the binding of DBD-A/B to a [$^{32}$P]ss-dT$_{12}$ substrate. Interestingly, when inhibition of the DBD-A/B construct were assessed, both the MCI13E and MCI13F compounds were completely ineffective on this protein construct.

Figure 5:
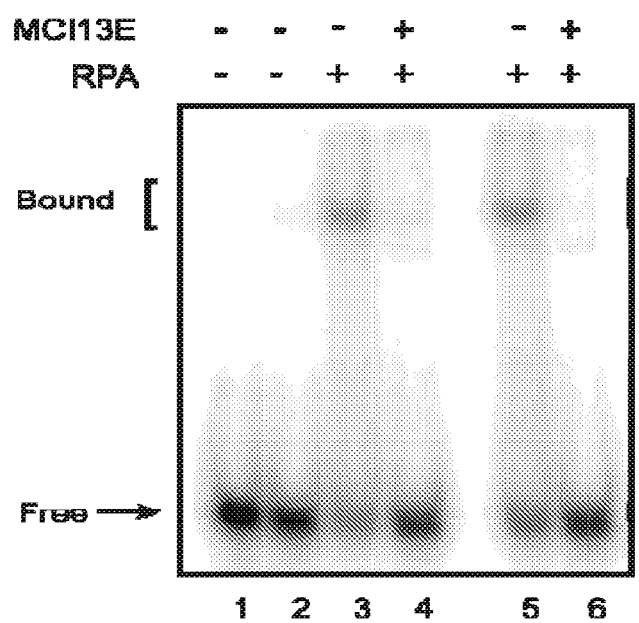
FIG. 5. Gel showing irreversible inactivation of full-length heterotrimeric RPA by MCI13E.

Considering the differential inhibition observed between the anhydride and halo esters with respect to specificity, experiments were carried out to determine if the isoborneol halo-esters inhibited full-length RPA in an irreversible fashion. Full-length RPA was mixed with MCI13E or vehicle control and the reaction mixtures were then dialyzed overnight. Referring now to FIG. 5. Gel showing irreversible inactivation of full-length heterotrimeric RPA by MCI13E. Incubation of RPA with MCI13E, dialysis and recovery was performed as described for FIG. 3. DNA binding activity of the resulting protein was assessed by EMSA using a 5'-[$^{32}$P]-ss 34-base DNA as described in "Methods". Lanes 1-4 pre-dialysis, lanes 5 and 6 post dialysis. Analysis of the resulting protein-DNA complex FIG. 5, lanes 5 and 6) showed that in reactions where RPA was incubated with MCI13E, inhibition was not reversed by dialysis as would be expected from a reversible inhibitor. In fact, the degree of inhibition was similar to that observed for the MCI13E treated RPA before dialysis (FIG. 5 lanes 3 and 4). These results indicate a mode of MCI13E inhibition of RPA that involved a covalent adduct between the MCI13E and RPA. These data suggest that the reduced reactivity of the ester derivatives provides a more specific interaction with RPA that potentially does not include the DBD-A/B region. These data demonstrate that MCI13E covalently label RPA which is of potential utility in measuring RPA and its inhibition by MCI compounds. This activity is consistent with MCI13E and F and their reaction with RPA serving as a pharmacodynamic marker of RPA inhibition or as a biomarker for RPA expression and activity.

The demonstration that MCI13E and MCI13F do not inhibit the DBD-A/B construct while showing potent inhibition of the full-length RPA heterotrimer point to other critical interactions between RPA and DNA that are essential for its DNA binding activity. While the elucidation of the specific sites of interaction of each SMI and RPA remains, the irreversible inactivation of full-length RPA by MCI13E provides a potential mechanism to identify the specific amino acids being modified and hence determine the subunit and potential DNA binding domain targeted by this SMI.

In order to study the specificity of the CheSS19, and MCI13E/F compounds, their effects on two ssDNA binding proteins which use OB-folds for recognition and binding of ssDNA, E. coli SSB (6) and the Schizosaccharomyces pombe Pot1(DBD) domain (11) were studied. The EcSSB protein is a non-sequence-specific ssDNA binding protein, whereas the SpPot1(DBD) protein is a telomere-specific, ssDNA binding protein. In these experiments, protein was pre-incubated with the SMIs, as was done for the RPA experiments, prior to addition of radiolabeled ssDNA to the reactions.

Figure 6A:
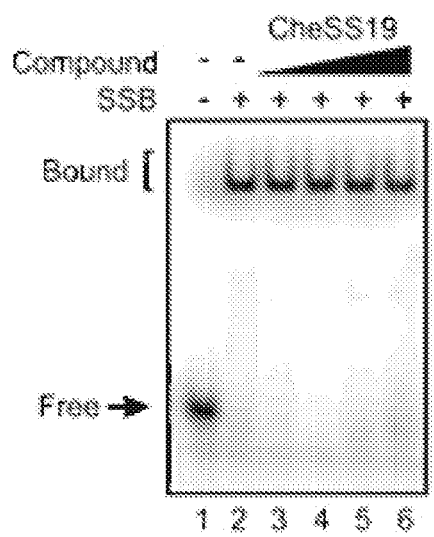
FIG. 6A. CheSS19 titration in EcSSB DNA-binding reactions.
Figure 6B:
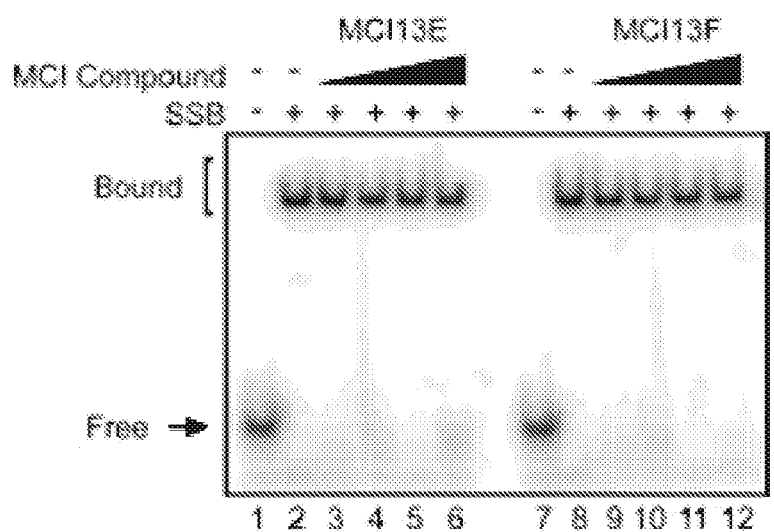
FIG. 6B. Titration of MCI13E and MCI13F in EcSSB DNA-binding reactions.

Referring now to FIG. 6B. CheSS19 titration in EcSSB DNA-binding reactions. CheSS19 (0, 25, 50, 100, and 200 μM) was pre-incubated with EcSSB and binding reactions were carried out. Referring now to FIG. 6C. Titration of MCI13E and MCI13F in EcSSB DNA-binding reactions. Concentrations of MCI13E/F used were: 0, 25, 50, 100, and 200 μM. In all panels, the 'Free' ssDNA is indicated with an arrow and the 'Bound' ssDNA is indicated by brackets. All reactions were performed in the same order and manner as the RPA binding reactions. EcSSB binding was unaffected by CheSS19 and the MCI13E and MCI13F compounds (FIGS. 6A and B).

Together, these data demonstrate that the RPA SMIs, CheSS19, and MCI13E/F are specifically inhibiting the interaction of RPA with ssDNA rather than acting as general ssDNA binding inhibitors or OB-fold interacting molecules.

The series of compounds based on a bicyclic isoborneol (MCI13E, MCI13F and CheSS19) showed inhibition of full-length heterotrimeric RPA. Interestingly the less reactive derivatives containing an ester (MCI13E and F) displayed no inhibitory activity in DNA binding assays with purified DBD-A/B while the more reactive anhydride derivative, CheSS19, showed potent inhibitory activity against both full-length RPA and the DBD-A/B construct. The mode of RPA inhibition with all of the isoborneol derivatives was found to be irreversible, consistent with the reactive anhydride and ester functional groups. None of the isoborneol compounds were found to significantly inhibit the ssDNA binding activity of EcSSB suggesting that this class of compounds is also specific for RPA. Together these data provide evidence suggestive of specific targeting of different functional domains of RPA that can be used to exploit and interrogate their importance in the various metabolic pathways in which RPA participates. Previous data demonstrated that inhibition of RPA with SMIs results in cell cycle arrest and sensitization to DNA damaging agents cisplatin and etoposide. These data suggest that exploitation of this chemical genetic approach can ultimately aid in the elucidation of the mechanism of RPA action in critical DNA metabolic pathways including DNA replication recombination and repair.

Figure 7A:
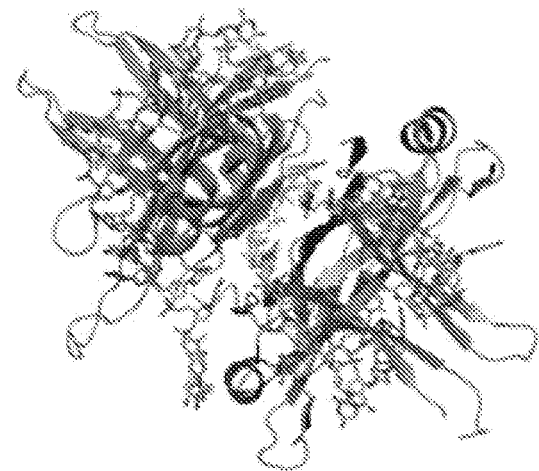
FIG. 7A.
Figure 7B:
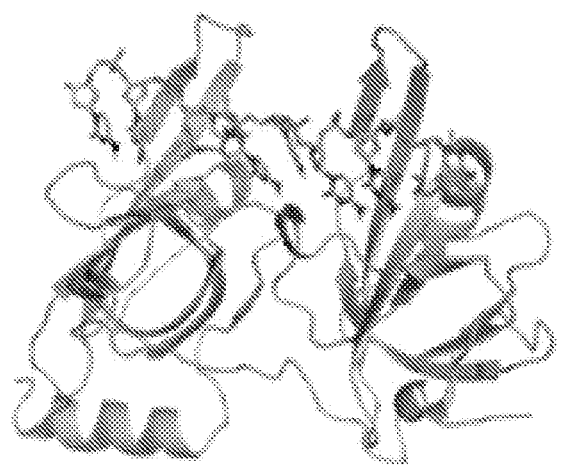
FIG. 7B. Structure of the RPA DBD-A/B (1JMC)(2)
FIG. 7C. Structure of the human Pot1(DBD) (1XJV)(3).
Figure 7C:
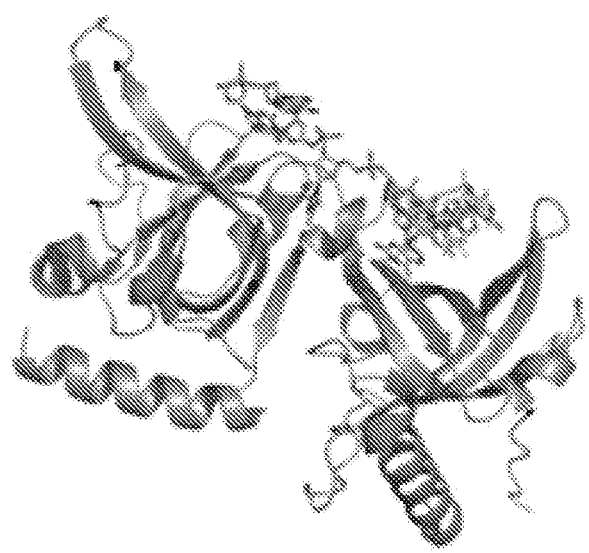

The results reported herein further demonstrate that MCI13E and F displays specificity for ssDNA binding activity of RPA as no significant inhibition of related ssDNA binding proteins, EcSSB or SpPot1(DBD) was observed. Although the EcSSB and SpPot1(DBD) proteins contain OB-folds, and in this regard, are structurally related to full-length RPA p70 and the DBD-A/B, the mechanism of ssDNA binding by these proteins is very different. Referring now to FIG. 7A. Model of the ssDNA-binding interface of OB-fold containing proteins. Proteins are shown as cartoon and ssDNA as stick renderings with C green, N blue, O red, and P orange. Structure of the homotetramer of EcSSB (1EYG)((12). Referring now to FIG. 7B. Structure of the RPA DBD-A/B (1JMC)(2) Referring now to FIG. 7C. Structure of the human Pot1(DBD) (1XJV)(3). Each structure is shown in the same orientation to highlight the different ssDNA binding interfaces used by each of these proteins for their specific functions. As shown in FIG. 7A, the EcSSB protein contains a single OB-fold, yet, forms a homotetramer yielding a functional molecule containing four OB-folds. The EcSSB protein also has been shown to bind nucleic acid in the reverse polarity compared to RPA (6). The series of compounds based on an isoborneol (MCI13E, MCI13F and CheSS19) showed inhibition of full-length heterotrimeric RPA. Interestingly the less reactive derivatives containing an ester (MCI13E and F) displayed no inhibitory activity in DNA binding assays with purified DBD-A/B while the more reactive anhydride derivative, CheSS19, showed potent inhibitory activity against both full-length RPA and the DBD-A/B construct. The mode of RPA inhibition with all of the isoborneol derivatives was found to be irreversible, consistent with the reactive anhydride and ester functional groups. None of the isoborneol compounds were found to significantly inhibit the ssDNA binding activity of EcSSB suggesting that this class of compounds is also specific for RPA. Together these data provide evidence suggestive of specific targeting of different functional domains of RPA that can be used to exploit and interrogate their importance in the various metabolic pathways in which RPA participates. Previous data demonstrated that inhibition of RPA with SMIs results in cell cycle arrest and sensitization to the DNA damaging agents, cisplatin and etoposide (1). These data suggest that exploitation of this chemical genetic approach can ultimately aid in the elucidation of the mechanism of RPA action in critical DNA metabolic pathways including DNA replication recombination and repair.

Still other compounds that interact with RPA have been identified and are characterized herein. This characterization includes studying the physiological effect of SMIs of the RPA-ssDNA interaction in a cell culture model. The isobornyl derivatives MCI13E and MCI13F demonstrated cellular activity and were chosen for further characterization. The data presented herein demonstrates that the disruption of RPA's activity in lung and ovarian cancer cell models results in increased apoptosis and lengthening of cell cycle stages. The induction of apoptosis is independent of p53 and these SMIs synergize with cisplatin in combination treatments.

Small molecule inhibitors have proved to be invaluable in the interrogation of biochemical pathways, protein activity and cellular function. While targeting macromolecular protein-protein and protein-DNA interactions is somewhat more complex than targeting an enzyme-substrate interaction, recent work has yielded some success in this regard This mechanism of inhibition is likely to impact all DNA metabolic events where RPA exerts its activity by high affinity binding to ssDNA. The demonstration that MCI13E and MCI13F do not inhibit the DBD-A/B construct while showing potent inhibition of the full-length RPA heterotrimer point to other critical interactions between RPA and DNA that are essential for its DNA binding activity. While the elucidation of the specific sites of interaction of each SMI and RPA remains, the irreversible inactivation of full-length RPA by MCI13E provides a potential mechanism to identify the specific amino acids being modified and hence determine the subunit and potential DNA binding domain targeted by this SMI. $IC_{50}$ values for MCI13E and MCI13F Measured in Different Cells.

Referring now to Table 1. Various esterified iso-borneol compounds according to FIG. 1I were tested for RPA inhibitory activity using the electrophoretic mobility shift in vitro DNA binding assay.

TABLE 1

Figure 1I:
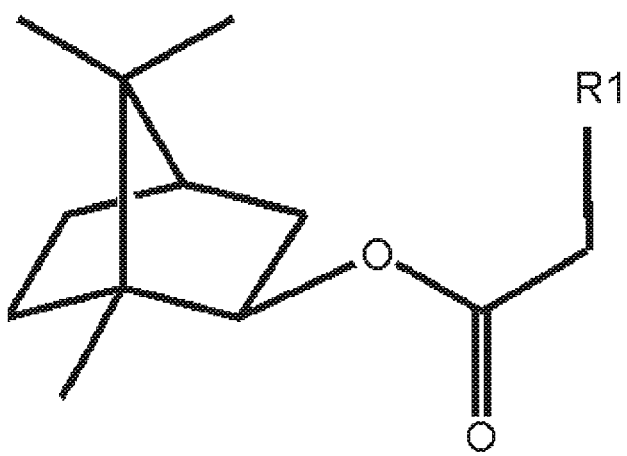
FIG. 1I. Structure of generic ester iso-borneol with R1 modified to impact ester reactivity.
Figure 1J:
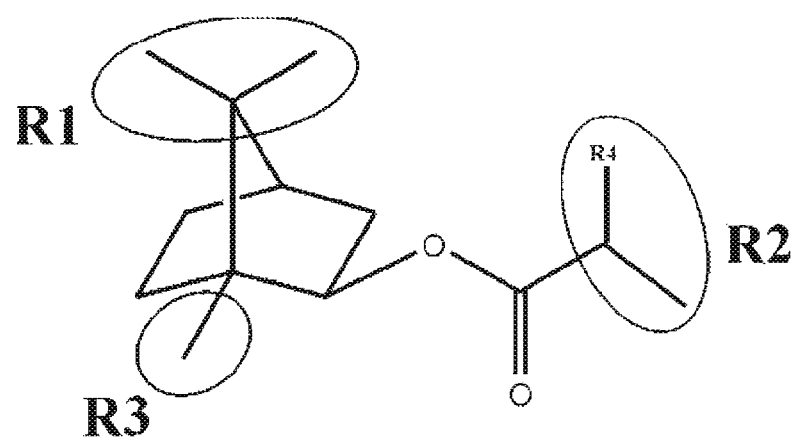
FIG. 1J. Structure of a generic ester iso-borneol positions of molecule that can be modified are indicated by R$_1$, R$_2$, R$_3$, and R$_4$.
Figure 2:
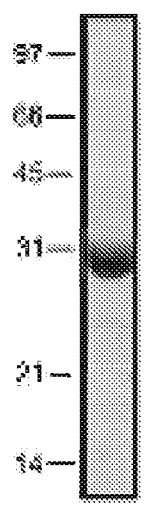
FIG. 2. SDS-PAGE analysis of purified RPA DBD-A/B.

Summary of activity data collected using selected compounds, Refers to $R_1$ in FIG. 1I.

| Compound Identifier | $R_1$ | Relative Inhibitory Activity |
| --- | --- | --- |
| MCI14A | H | – |
| MCI13B | CH3 | – |
| MCI13D | CL | – |
| MCI13E | Br | +++ |
| MCI13F | I | +++ |

Referring now to Table 2. The effect of MCI13E and MCI13F on different cell lines was measured both compounds had $IC_{50}$ values in the rage of about 5 µM against A549 and H 460 cells.

TABLE 2

Summary of $IC_{50}$ values measured for two different halo-esters of isoborneal in two different cell lines. These data were collected after by measuring cell viability 48 hours after exposing the cells to the compounds.

| Cell Line | $IC_{50}$ with MCI13E Treatment | $IC_{50}$ with MCI13F Treatment |
| --- | --- | --- |
| A549 | 5 uM | 5 uM |
| H460 | 5 uM | 4 uM |

Referring now to Table 3. The effect of MCI13E and MCI13F on different H1299 cells was measured both compounds had $IC_{50}$ values in the rage of about 0.5 µM against these cells. These data demonstrate these compounds are effective inhibitors of cancer cell growth.

TABLE 3

Summary of $IC_{50}$ values measured for two different terpene derivatives in H1299 cells. These data were collected after by measuring cell viability 25 hours after exposing the cells to the these compounds.

| Cell Line | $IC_{50}$ with MCI13E Treatment | $IC_{50}$ with MCI13F Treatment |
|---|---|---|
| H1299 | 0.5 uM | 0.5 uM |

SMIs of RPA's DNA binding activity decrease cell viability, induce apoptosis and lengthen cell cycle stages—Previous work identified and characterized the in vitro activity of MCI13E (FIG. 1B), a SMI of RPA which blocks the RPA-DNA interaction (1,10). Considering RPA in an essential protein which plays a central role in DNA replication was assessed the activity of the SMI MCI13E in assays measuring cellular viability.

Figure 8:
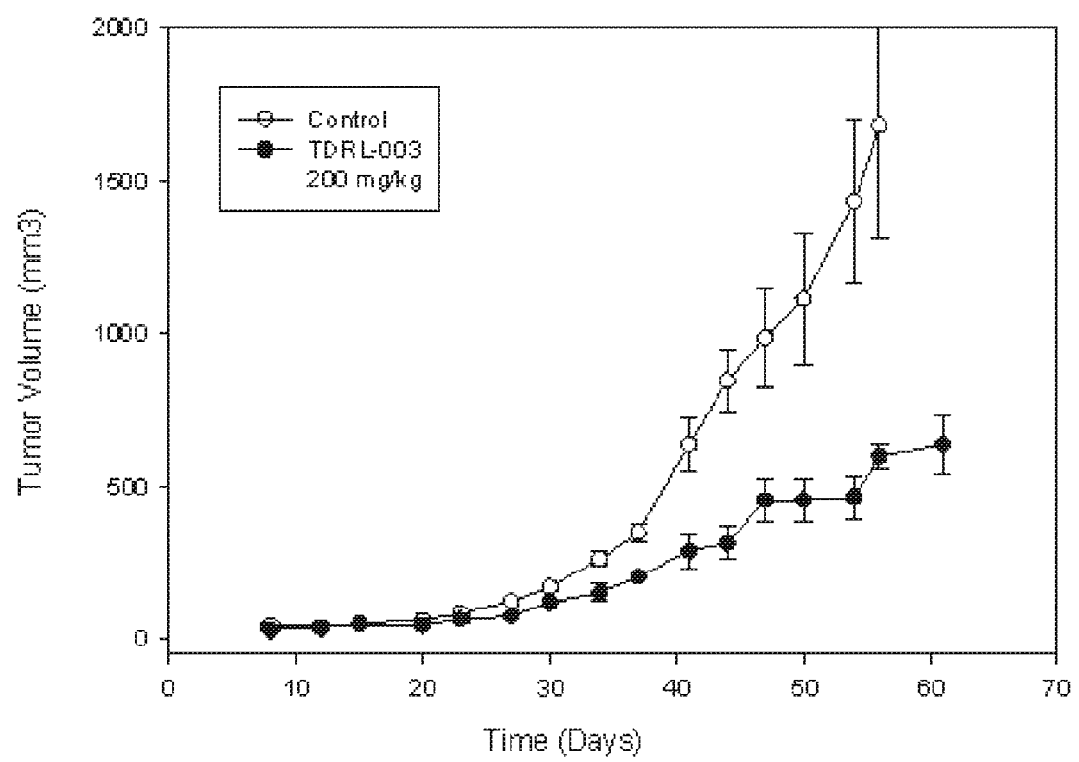
FIG. 8. Graphs of tumor volume versus number of days after treatment with either control or 200 mg kg$^{-1}$ of TDRL-003.

The in vivo activity of the TDRL-003 class of RPA inhibitors was assessed. Data on the cellular activity of the TDRL-003 class of irreversible RPA inhibitors demonstrated induction of classical apoptosis and an $IC_{50}$ in the low μM range. To determine if TDRL-003 treatment and inhibition of RPA-DNA binding activity is a viable therapeutic strategy, the toxicity of this compound was determined in naive NOD/SCID mice. No toxicity was observed up to 200 mg/kg while increasing the doses to 400 and 800 mg/kg did result in morbidity. The efficacy of this compound was also measured in an ectopic human NSCLC xenograft in NOD/SCID mice and treated at 200 mg/kg with the dosing regimen NSCLC were implanted in the hind flanks of NOD/SCID mice and when the tumors reached 100 mm$^3$, mice were randomized to treatment with either TDRL-003 or vehicle control. Dosing was twice a week for two weeks starting at week three. Tumor size was monitored throughout the experiment. Referring now to FIG. 8. The results presented in FIG. 8 demonstrate a significant reduction in tumor growth with TDRL-003 treatment. These very exciting results lay the ground work for pursuing this class of inhibitors in NSCLC. In addition, the MCI derivatives show greater inhibitory activity compared to TDRL-003 suggesting even greater efficacy is possible though this will have to be weighed against any potential increase in toxicity. The irreversible mechanism of RPA inactivation also holds the potential for the in vivo analysis of target inactivation by detecting alkylated RPA in MCI13E treated mice.

Figure 11A:
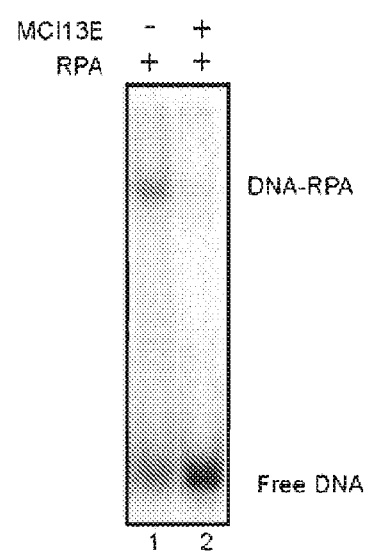
FIG. 11A. Gel showing effect of MCI13E on DNA-RPA binding.
Figure 11B:
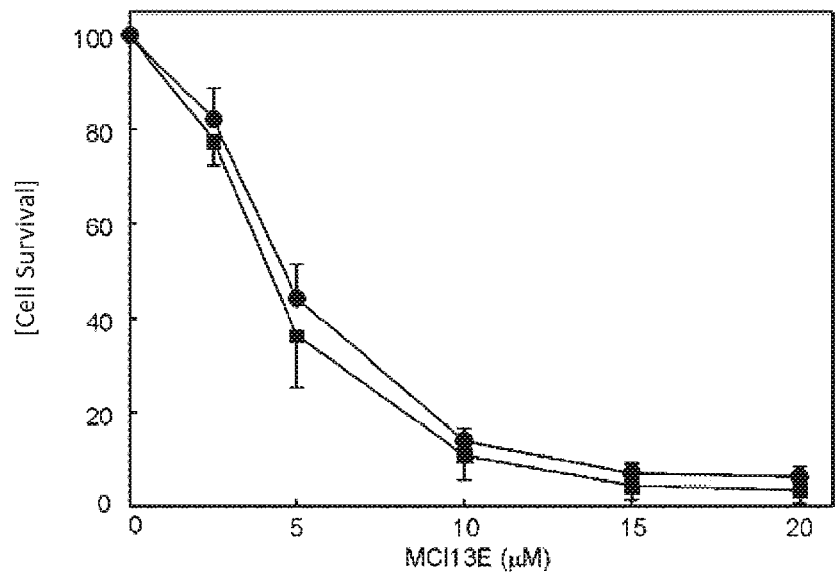
FIG. 11B. Graph of cell viability measured as a function of [MCI2E].
Figure 11C:
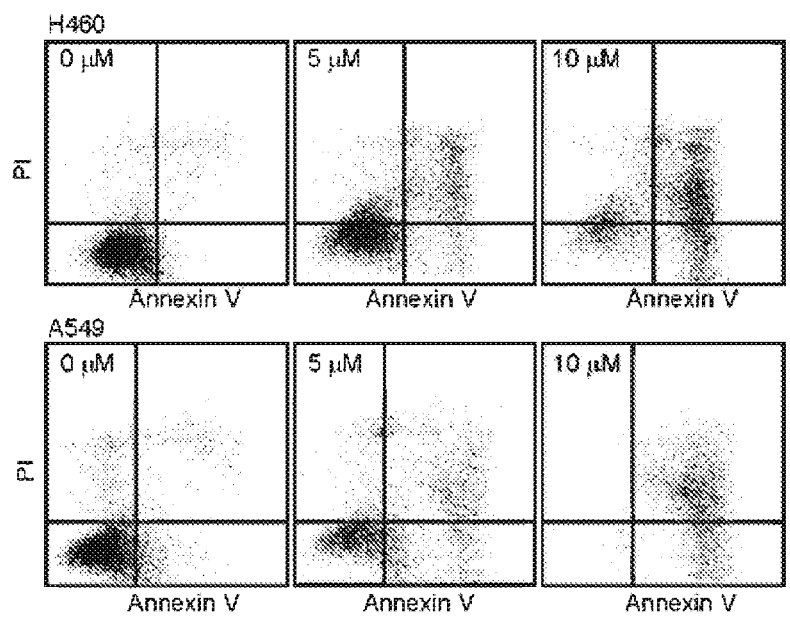
FIG. 11C. Graph of MCI13E induced death via apoptosis in NSCLC cell lines.
Figure 11D:
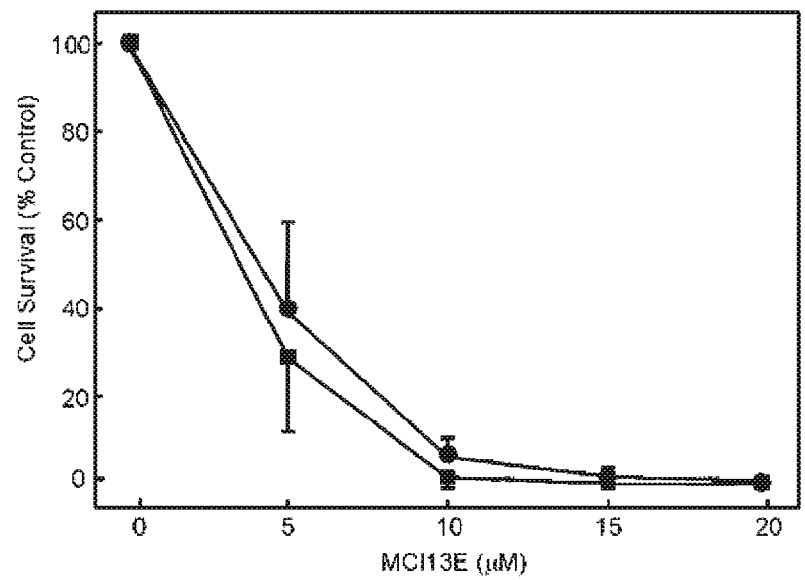
FIG. 11D. Graph of cell survival as a function of [MCI1EC].

Referring now to FIG. 11A. Gel showing effect of MCI13E on DNA-RPA binding. Lane A MCI13E, lane B) MCI13E inhibits RPA-DNA binding in vitro. RPA was mock treated (lane 1) or treated with MCI13E (50 μM) (lane 2) and DNA binding to a single stranded 30 bp DNA (12.5 nM) assessed by EMSA analysis as previously described by Anciano et al. Referring now to FIG. 11B, MCI13E displays single agent cytotoxic activity against A549 (squares) and H460 (circles) NSCLC cells. Cytotoxicity was analyzed via crystal violet analysis as described in "methods" 48 hours following MCI13E treatment. Data represent the average and standard deviation of four replicate experiments with each replicate containing triplicate determinations and the circles represent data from H460 cells and squares A549 cells. Referring now to FIG. 11C. Graph of MCI13E induced death via apoptosis in NSCLC cell lines. Cell were treated with the indicated concentrations of MCI13E for 48 hours and analyzed for the induction of apoptosis via Annexin V/PI staining Referring now to FIG. 11D. Graph of cell survival as a function of [MCI1EC]. Percent survival was calculated for each cell line using untreated cells as a control. Data presented are the average and standard deviation from four replicate experiments. Experiments were performed in non-small cell lung cancer (NSCLC) cell lines A549 (squares), an adenocarcinoma, and the large cell carcinoma H460 cell line (circles). Both lung cancer cell lines displayed a decrease in viability with increasing concentrations of SMI (FIG. 13B), with similar sensitivity and $IC_{50}$ values of approximately 5 μM.

Figure 18:
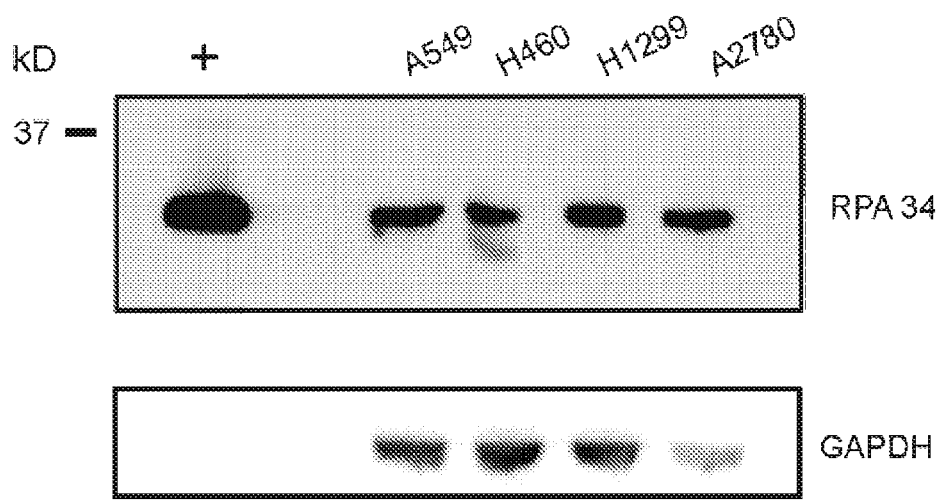
FIG. 18. Blot showing Endogenous Levels of RPA.

Referring now to FIG. 18. Blot showing Endogenous Levels of RPA. Each cell line analyzed were plated (3×10$^6$) in 10 cm dishes and allowed to adhere overnight. Following a 5 ml PBS wash the cells were scraped into 100 μl of RIPA buffer. Cell extracts (40 μg) were loaded onto 10% SDS-PAGE gels, transferred to nitrocellulose membranes and probed for the presence of RPA34. Purified RPA was used as a positive control while GAPDH was probed for a loading control. No change in the levels of endogenous RPA as a function of MCI13E treatment was detected (FIG. 18).

To determine the cellular mechanism by which apoptosis is induced by SMI treatment, the effects on cell cycle progression was assessed. Interestingly treatment of A549 cells with increasing doses of MCI13E produced a greater proportion of cells in the G1 phase of the cell cycle whereas H460 cells demonstrate an increase in the proportion of cells in S-phase (FIG. 14). Cell cycle progression was analyzed at 6, 12, and 24 hours of treatment with increasing concentrations of SMI and the 6 and 12 hour time points are presented in FIG. 13D. While cell cycle stages lengthened by 6 hours, there is no significant further increase after an additional 6 or 12 hours of treatment (FIG. 13 and data not shown). This suggests that the effect of MCI13E occurs early and does not persist. This may also be due to chemical instability of the α-haloester moiety of MCI13E, resulting in reduced activity.

Figure 13A:
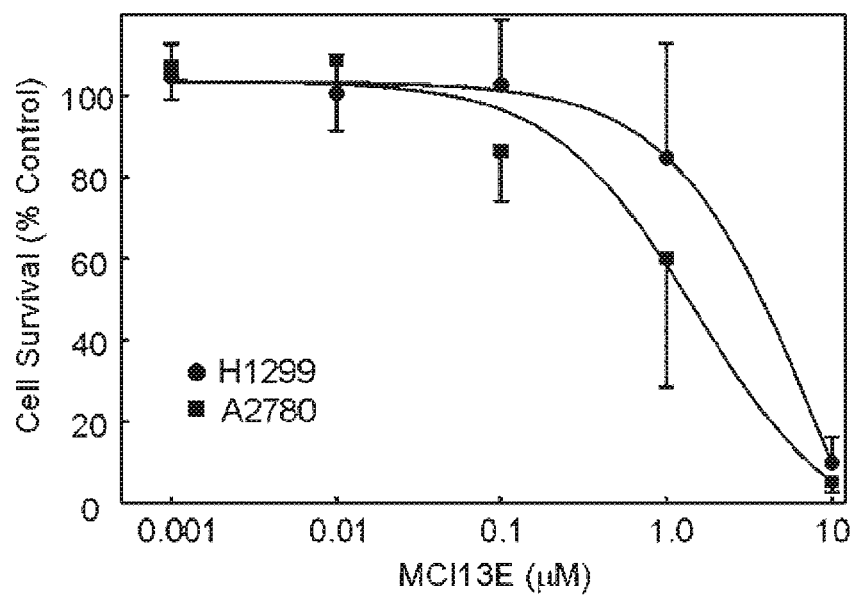
FIG. 13A. Graph of H1299 and A2780 cell survival as a function of [MCI13E].
Figure 13B:
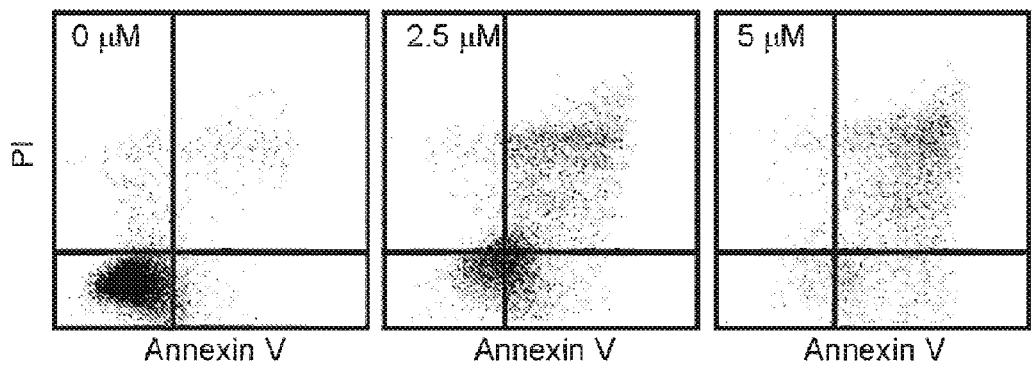
FIG. 13B. H1299 cells were analyzed for the induction of apoptosis via Annexin V and propidium iodine staining.
Figure 13C:
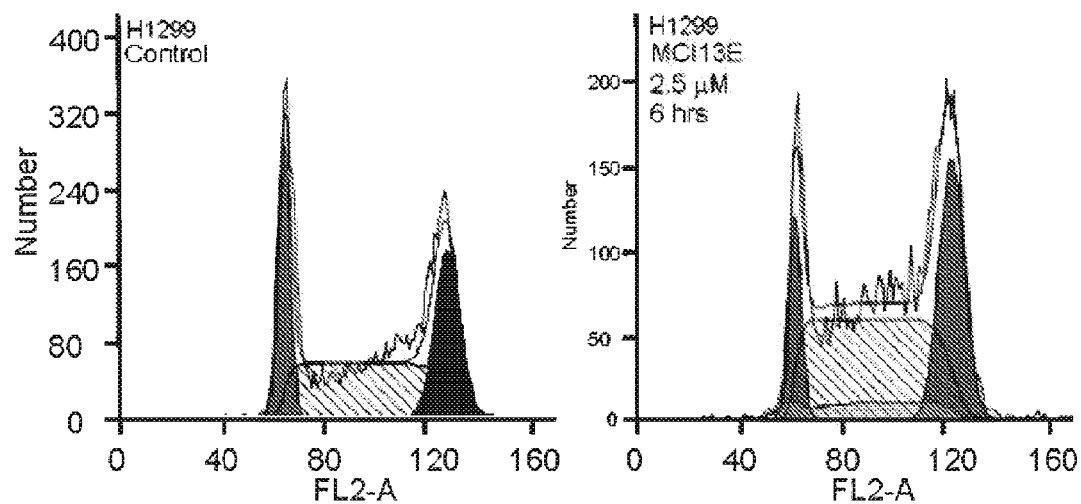
FIG. 13C. Cell cycle analysis conducted in H1299 cells; following 6 hours of treatment cells accumulate in the S-phase of the cell cycle.
Figure 13D:
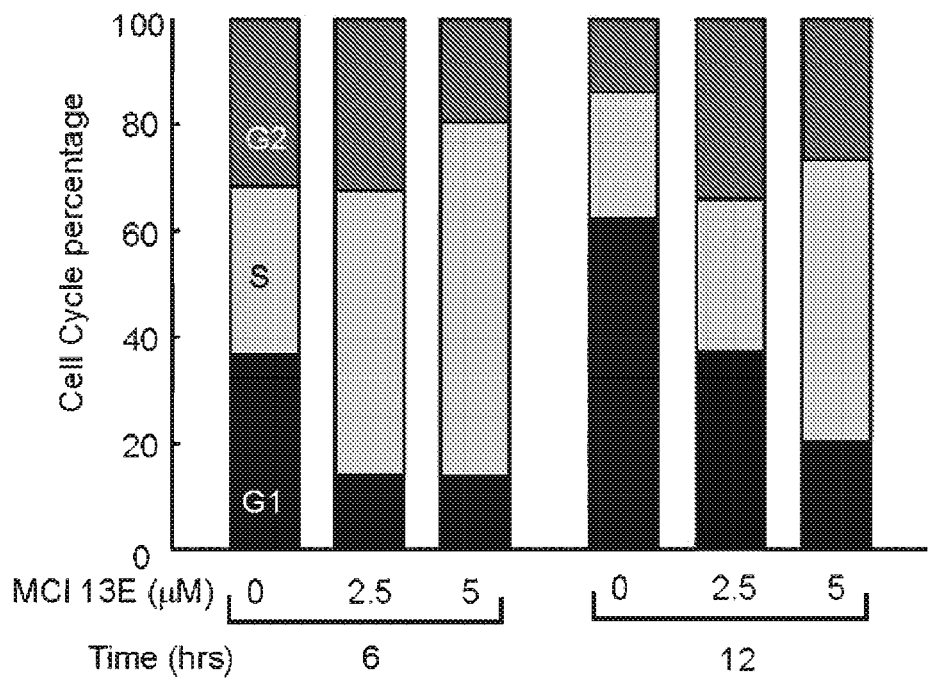
FIG. 13D. Cell Cycle Analysis after sequential treatment with a combination of Cisplatin and MCI Treatment.
Figure 14A:
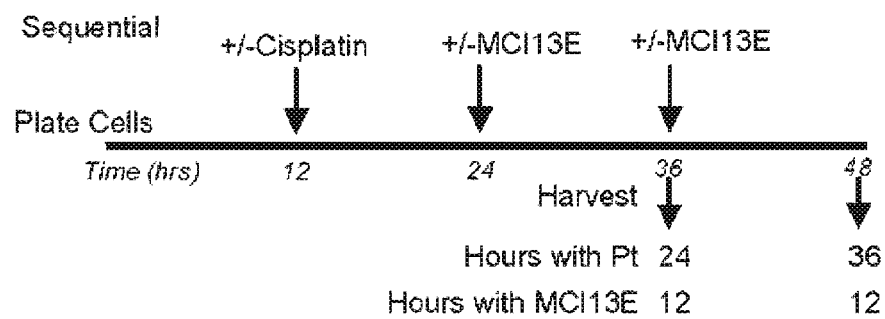
FIG. 14A. Schematic showing sequential treatment of cells using cisplatin and MCI13E.

Considering this difference in cell type, the effects of MCI13E on other cell types was measured. The p53 null NSCLC cell line H1299 and the epithelial ovarian cancer cell line A2780 were selected. MCI13E was highly potent against A2780 cells with an $IC_{50}$ of approximately 1 μM while the H1299 cell line displayed a similar $IC_{50}$ (~4 μM) to the other NSCLC cell lines despite the p53 status (FIG. 13A). Also note that this $IC_{50}$ was determined following 24 hours of treatment, similar to that of the A2780 cell line, again demonstrating sensitivity to the SMI. Cell cycle progression was also measured in the H1299 cell line following 6, 12, and 24 hours of treatment with MCI13E and an increased percentage of cells accumulated in S-phase (FIG. 13D). As with the H460 cell line, an additional 6 or 12 hour of treatment did not result in a significant increase in the percentage of cells accumulating in S-phase.

Because of its essential rose in cell survival NER provides an attractive target for drug design. Compounds that have been developed to target components of this system include Cisplatin. Cisplatin, (cis-diamminedichloroplatinum[III]), is a front-line treatment for a variety of neoplasms, including ovarian, lung and testicular cancers (13) Innate and acquired resistance to cisplatin therapy is a recurring issue in the clinic and a wide spectrum of responses are observed in cancer patients, warranting the discovery of novel chemotherapeutic treatments. Cisplatin induces it toxic effects by interacting with DNA, typically by intrastrand linkage of adjacent guanines (GpG). This produces an N—Pt—N cross-link from the imidazole nitrogens (N7), resulting in a 12-28° kink in the DNA. This kink is then recognized and repaired by the NER machinery (10). Disruption of protein-DNA interactions, resulting in a decrease in NER efficiency and DNA repair, may be exploited to increase efficacy of cisplatin and related platinum chemotherapeutics. Previous work has demonstrated that a decrease in NER efficiency elicited by decreasing the expression of essential NER proteins, resulting in increased sensitivity to cisplatin. Therefore targeting the RPA-ssDNA interaction via SMIs holds the potential to sensitize cancer cells to Pt-based chemotherapy. Combination treatments involving SMIs may result in increased accumulation of cisplatin adducts and therefore increased efficacy of treatment, potentially decreasing the probability of recurrence/resistance.

Cisplatin damage results in a cell cycle response arresting cells in the G2 phase ultimately leading to cellular apoptosis. The P53 tumor suppressor is a key element in DNA damage response. It is post-translationally modified upon the induction of DNA damage resulting in activation. Activated p53 transactivates the p21 cyclin-dependent kinase inhibitor which in turn results in cell cycle arrest. In the absence of the ability to repair the lesions, ultimately apoptosis can be induced. Therefore, decreasing NER catalyzed removal, via inhibition of the RPA-DNA interaction, may result in persistent cisplatin-DNA adducts and increased cellular sensitivity to cisplatin treatment.

Synergy with cisplatin—Analyses thus far indicate that inhibition of RPA is effective in eliciting effects consistent with inhibition of RPAs role in cell cycle progression and DNA replication. To assess if SMI treatment impacts RPAs role in DNA repair, how MCI13E or MCI13F treatment influences cellular sensitivity to cisplatin was assessed. MCI13F is an terpene derivative, MCI13F demonstrates an $IC_{50}$ similar to that of MCI13E in vitro (10) and in cell culture models of NSCLC (14) shown) but contains an iodide in place of the bromide. Cisplatin-induced DNA damage is primarily repaired via NER and homologous recombination. Considering that both cisplatin and MCI treatment possess single agent activity in the NSCLC cell lines, combination index studies were used to analyze the effectiveness of combination treatments. Initially, a concurrent approach, similar to that described for another RPA SMI, TDRL-505 (1) was used. Briefly, A549 cells were treated for 48 hours with MCI13E, cisplatin, or combination treatment, with viability determined via crystal violet staining. The results from these experiments revealed an antagonistic effect (Table 4) suggesting that either cisplatin was rendering the SMI ineffective or vice versa. The analysis of cell cycle effects induced by MCI suggested that this compound may have a relatively short half-life eliciting its effects relatively quickly, while cisplatin typically requires at least 48 hours in order to produce an observable effect. Next, a sequential treatment protocol was used, first treating cells with cisplatin for 24 hours, then adding the SMI and incubating for an additional 24 hours. The results from these experiments displayed synergy based on the Chou-Talalay method (15). Interestingly, slight differences with MCI13E, synergizing with cisplatin at higher dosing concentrations while MCI13F demonstrated synergy with cisplatin at all tested concentrations was observed (Table 4).

TABLE 4

Schedule dependent MCI-cisplatin synergy

| Treatment | % affected | CI Sequential | CI Concurrent |
|---|---|---|---|
| MCI 13 E/Pt | 0.2 | 0.65 | 0.94 |
| | 0.5 | 0.79 | 1.9 |
| | 0.75 | 0.86 | 3.0 |
| MCI 13F/Pt | 0.2 | 0.38 | 2.1 |
| | 0.5 | 0.50 | 3.7 |
| | 0.75 | 0.51 | 5.2 |

Cell cycle analysis of combination treatments demonstrates a difference in cycle lengthening—As noted herein, MCI13E synergizes with cisplatin following sequential treatment while concurrent cisplatin/SMI treatment results in an antagonistic effect. Knowing that MCI13E induced a lengthening of the G1 stage of the cell cycle for A549 cells, it was of interest to determine if alteration in cycle progression with either sequential or concurrent cisplatin/SMI treatment could account for the differences in drug interactions. A549 cells were plated and treated sequentially or concurrently with cisplatin/SMI and processed for cell cycle analysis. The experiment was performed using two separate dosing schedules one keeping the time of SMI treatment consistent between the sequential and concurrent schedules and the other keeping cisplatin treatment time consistent. The data from the latter experiment is presented (FIG. 14) using a reduced dose of SMI corresponding to the CI studies and demonstrates, under both schedules, the cisplatin induced S and G2 accumulation at 24 and 36 hours post treatment is modestly impacted by SMI treatment. These results suggest that differences in cellular response to the combined treatment schedule are not a function of differential cell cycle arrest between the concurrent and sequential dosing schedules.

Figure 19A:
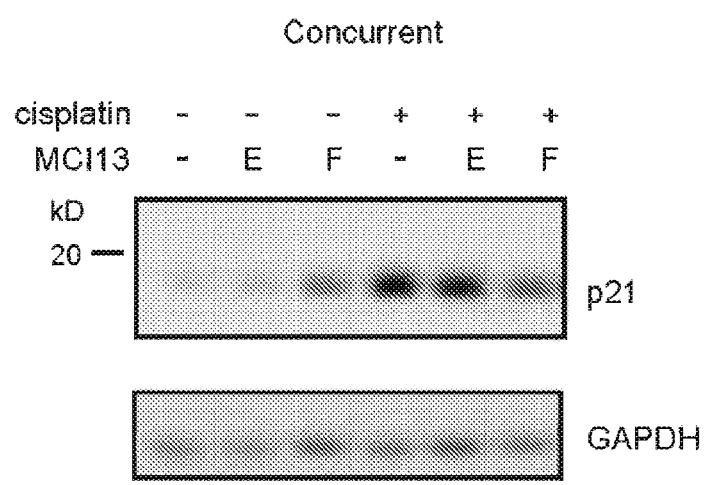
FIG. 19A. Blot of total Protein Expression Following Concurrent Treatment.
Figure 19B:
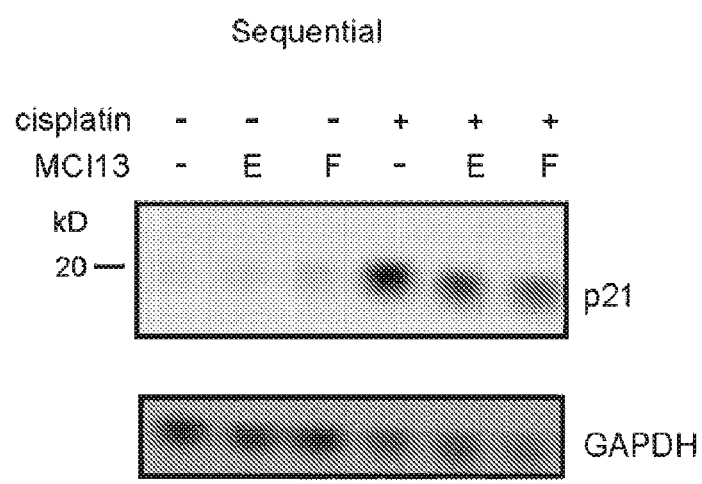
FIG. 19B. Blot of total protein following sequentially treatment with cisplatin (5 µM) and MCI13E or MCI13F for 24 total hours.
Figure 19C:
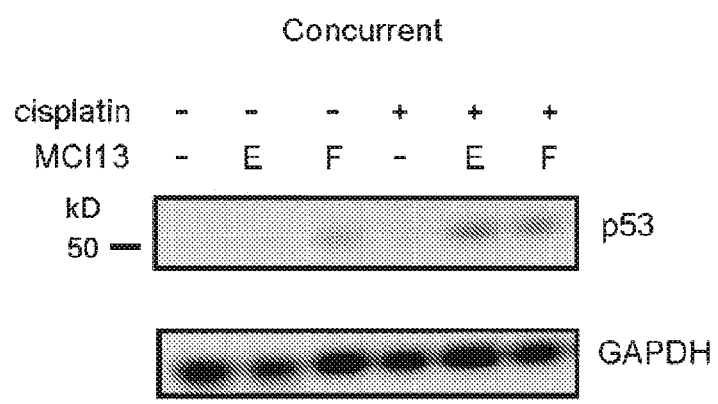
FIG. 19C. Blot of p53 GAPDH level after concurrent treatment with cisplatin and MCI13E.

Transcriptional and Post-Translational Modifications following combination SMI and cisplatin treatments—While no significant alteration in cell cycle progression was observed how activation of the DNA damage signaling pathways were impacted by the two treatment protocols was determined. QPCR was used to analyze the transcriptional activation of a series of genes encoding proteins involved in the DNA damage response (DDR). Three of these XPC, DDB2 and p21 showed consistent increases in expression in cisplatin treated cells as expected for p53 responsive genes. Interestingly in the concurrently treated cells, the expression of each gene was reduced compared to the cisplatin control while in the sequentially treated cells, only p21 showed a decrease in expression compared to the cisplatin control. This QPCR data was further confirmed by western blot analysis of p21 expression following the various treatment methods (FIG. 19). This suggests that p53 is differentially activated without a corresponding change in cell cycle distribution (FIG. 15).

Figure 16A:
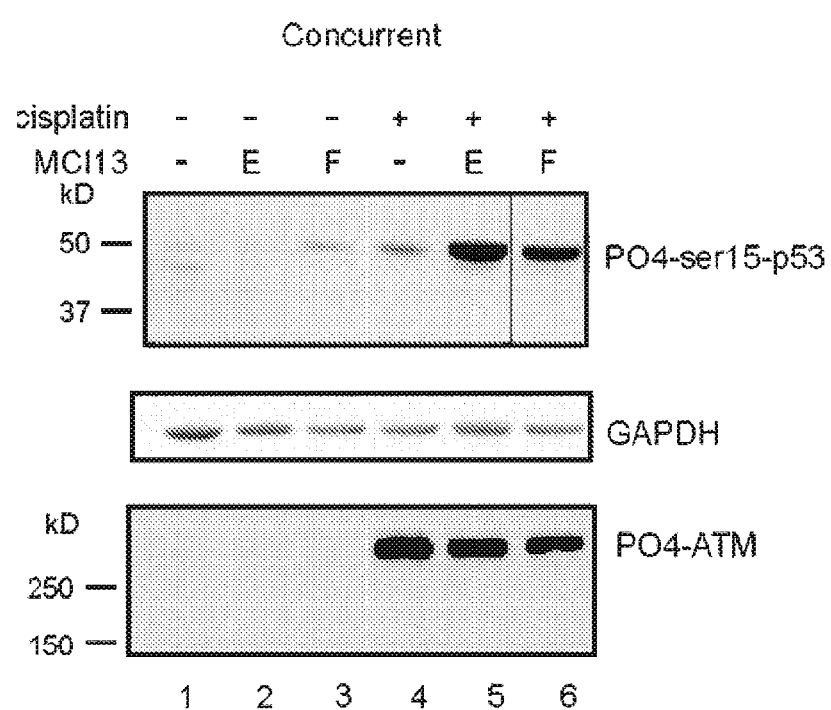
FIG. 16A. A Western Blot Analysis of cells following concurrent treatment with cisplatin and MCI13E or F.

To assess p53 activation directly, determined the phosphorylation level of serine-15 was determined using the differing combination treatment protocols. Interestingly, bromide MCI13E and the iodide MCI13F had minimal single-agent effects on p53 phosphorylation while concurrent treatment with cisplatin produced a dramatic increase (FIG. 16A). This increase was not seen in the sequentially treated cells and is consistent with the transcriptional profiling analysis where differences were observed depending on treatment schedule. Analysis of total p53 was also analyzed, via western blot analysis, and a similar increase in total protein following concurrent treatment was observed. Referring now to FIG. 19B, Lysates were probed for p21 (A and B) or p53 (C) and GAPDH was probed as a loading control in each experiment. Following sequential treatment, however, total p53 was below the detection limit which could be attributed to the difference in treatment times and the half life of p53 (FIG. 19). A series of factors including DNA dependent protein kinase (DNA-PK), Ataxia-telangiectasia mutated and Rad3-related (ATR) kinase, ataxia-telangiectasia mutated (ATM) kinase, checkpoint kinase-1 (CHK1) and checkpoint kinase-2 (CHK2 were assessed). Robust levels of phosphorylation and activation was observed only for ATM and in this case there was no significant difference between the concurrent sequentially treatments, suggesting that the differential activation of p53 was not applicable to ATM.

Targeting protein-DNA interactions with small molecules holds the potential to disrupt numerous essential cellular processes that could be used therapeutically. This approach holds much promise but presents significant challenges. Advances in screening technologies including high throughput screening and in silico screening of chemical libraries has aided in the identification of SMIs of a small number of protein-DNA interactions. Two different classes of SMIs capable of inhibiting the interaction of RPA with DNA were identified (1,10). Disclosed herein are the cellular effects of a novel isoborneol haloacetate SMI (MCI13E), which irreversibly inhibits RPA binding to ssDNA in vitro. Another RPA inhibitor, TDRL-505, a reversible inhibitor that disrupts RPA binding through the p70 central OB-fold-DNA interaction (1,10) was recently reported. However, MCI13E does not act via the p70 central DNA binding domain A/B. Considering that MCI13E and TDRL-505 target two distinct regions of RPA (10) it is not surprising that some different cellular effects of treatment with these compounds was observed. Both MCI13E and TDRL-505 possess single agent cytotoxic activity likely owing to RPA's role in S-phase replication. However, MCI13E treatment induces death via classical apoptosis (FIG. 11) while TDRL-505 is cytotoxic via a non-apoptotic pathway (1). Furthermore, the $IC_{50}$ values associated with single agent treatment of A549 and H460 cells lines with MCI13E is lower than that following treatment with TDRL-505. Interestingly genetic knockdown of RPA p70 resulted in an increase in sub-G1 cells suggestive of apoptosis which was preceded by an accumulation of cells in S-phase (16) consistent with the MCI13E inhibitor data. Depending on cell type, either an in increase in G1 or S-phase cells following MCI13E treatment (FIGS. 12, 13, and 14) is observed.

Figure 12A:
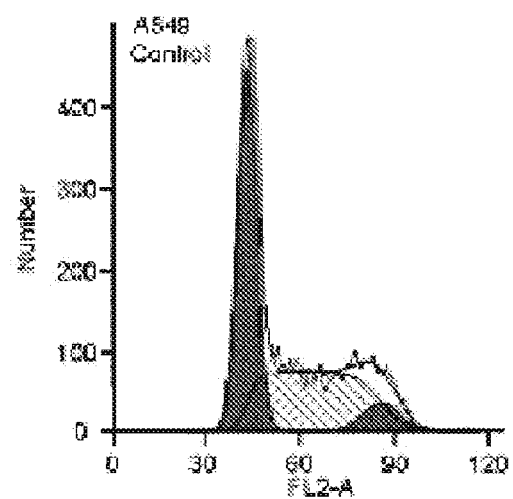
FIG. 12A. Cell Cycle Analysis of Lung Cancer Cell Lines (A549 cells) following Treatment with MCI13E.
Figure 12B:
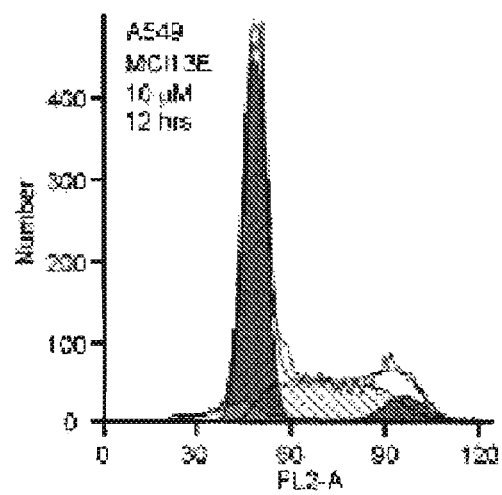
FIG. 12B. Cell Cycle Analysis of Lung Cancer Cell Lines (A549 cells) following Treatment with MCI13E.
Figure 12C:
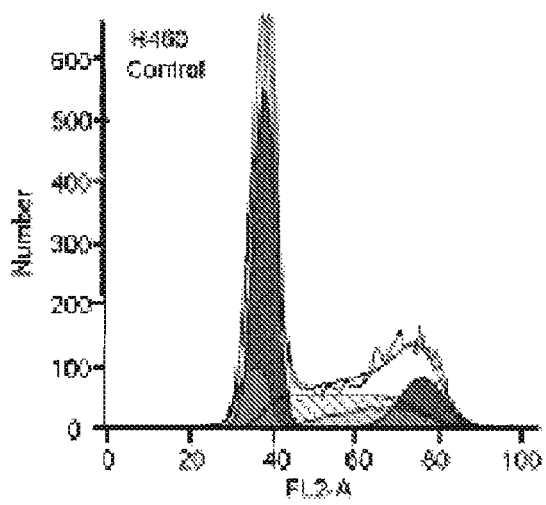
FIG. 12C. Cell cycle distribution of H460 cells after treatment as indicated and analysis using P1 staining and flow cytometry.
Figure 12D:
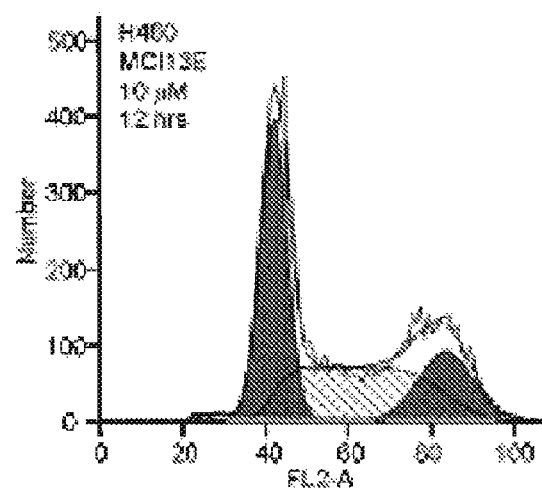
FIG. 12D. Cell cycle distribution of H460 cells after treatment as indicated and analyzed using P1 staining and flow cytometry.
Figure 12E:
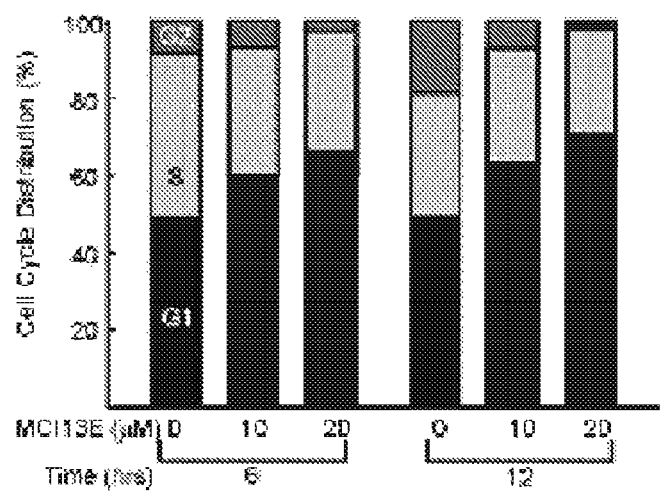
FIG. 12E. Bar graph showing the effect of MCI13E on cell cycle distribution.
Figure 12F:
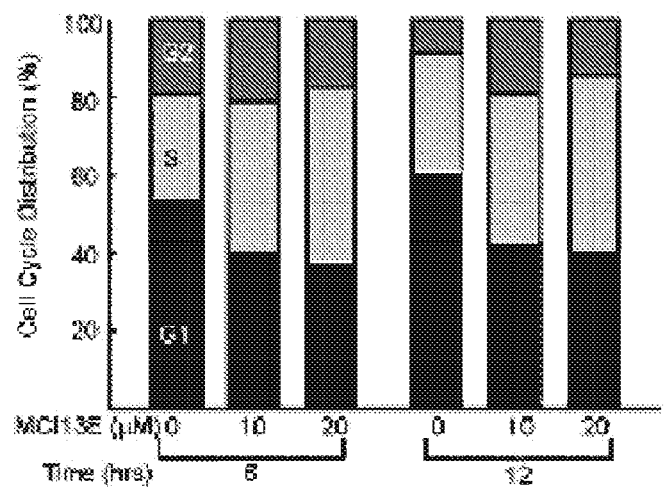
FIG. 12F. Bar graph showing the effect of MCI13E on cell cycle distribution.

Referring now to FIG. 12A and FIG. 12B. Cell Cycle Analysis of Lung Cancer Cell Lines Following Treatment with MCI13E. A549. Referring now to FIG. 12C, and FIG. 12D. H460 were treated as indicated and analyzed for the cell cycle distribution using PI staining and flow cytometry. Quantification of data following 6 hours and 12 hour treatment with 10 and 20 µM MCI13E was performed for both A549 (FIG. 12E) and H460 (FIG. 12F) Data presented represent the averages of three replicate experiments.

Figure 14B:
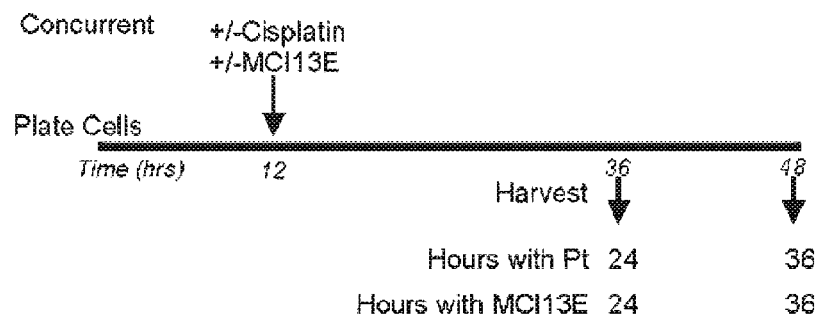
FIG. 14B. Schematic showing concurrent treatment regimen for maintaining constant cisplatin treatment time.
Figure 14C:
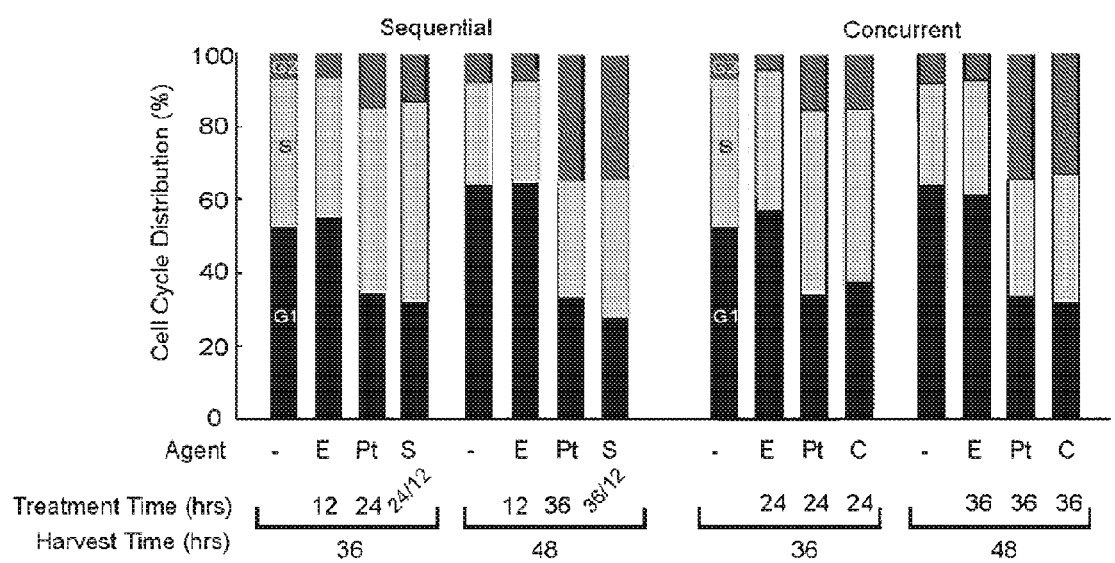
FIG. 14C. Bar graph showing the cell cycle of cells treated with, cisplatin and MCI17E.

Referring now to FIG. 13A. Cell Viability and Apoptosis of Ovarian and p53 null Lung Cancer Cell Lines. A) Ovarian cancer cell line A2780 and the p53 null lung cancer cell line, H1299, were treated with log dosing of MCI13E and viability analyzed via CCK-8 metabolic assay as described in Methods. Data is presented as cell survival which was determined as a percent of the untreated control cells and represents the average and standard deviation of triplicate experiments Referring now to FIG. 13B. H1299 cells were analyzed for the induction of apoptosis via Annexin V and propidium iodine staining A shift to the upper right quadrant was observed and is indicative of the induction of apoptosis Referring now to FIG. 14A. Schematic showing sequential treatment of cells using cisplatin and MCI13E. Referring now to FIG. 14B. Schematic showing concurrent treatment regimen for maintaining constant cisplatin treatment time. Referring now to FIG. 14C, A549 cells were treated sequentially or concurrently with single agent or combination treatments of cisplatin denoted "Pt" and/or MCI13E (denoted "E") and analyzed for cell cycle distribution via PI and flow cytometry. Data represents the average percentage of cells in G1, S, or G2 phase of the cell cycle. This experiment was repeated twice with similar results.

This difference in the cell cycle phase lengthening following treatment may be due to the difference in initial cell cycle distribution and may be magnified due to this initial difference. It is easy to attribute the differential effects of these two classes of compounds to the different mechanisms by which they inhibit RPA. However, potential of off-target effects or differential activity as a function of compound stability and/or cellular uptake cannot be ruled out.

In addition to single agent cytotoxic activity, inhibition of RPA results in increased sensitivity to cisplatin (FIG. 14 (1)). RPA's role in NER is twofold. First RPA interacts with damaged duplex DNA and forms the pre-incision complex with XPA and TFIIH (17). Second RPA aids in the resynthesis and relegation in the final step of the NER pathway (18). More recently, mutational analysis of RPA has revealed differential effects on DNA repair activity, sometimes producing a dramatic reduction in ss-DNA binding and abrogating repair, but with less of an effect on replication (16). Consistent with the importance of ssDNA binding in repair, a greater than additive effect when combining MCI13E treatment with cisplatin was observed. Interestingly, this is a schedule-dependent phenomenon, and synergy was only observed in cells treated sequentially with cisplatin then MCI13E. Schedule dependent synergy was not observed for TDRL-505 cisplatin interactions (1). The schedule-dependent synergy of MCI13E could not be attributed to alterations in cell cycle, but could point to compound stability and reactivity, as the haloester may be relatively unstable in medium. The potential also exists for a direct MCI13E-cisplatin interaction which inactivates either or both compounds.

Recent studies have also demonstrated RPAs role in DNA damage induced signal transduction through the ATR-interacting protein (ATRIP) which in turn initiates the recruitment of ATR (19,20). The formation of this complex and the activation of ATR by TOPBP1 results in the phosphorylation of CHK1, which can phosphorylate p53 to block cell cycle progression to allow time for the repair of damaged DNA (19). While the low levels of endogenous CHK1 precluded definitive analysis, p53 activation was assessed and differential phosphorylation was observed in cells which were subject to concurrent versus sequential cisplatin-MCI13E treatment. These data suggest that the synergy observed in sequential treatment could be a function of reduced p53 activation compared to that observed with the concurrent treatment (FIG. 16). Similarly, the dramatic increase in p53 activation in the concurrent treatment is likely in part responsible for the significant antagonism observed between cisplatin and MCI in the concurrent treatment protocol (Table 4).

Interestingly, single agent treatment with SMIs MCI13E or MCI13F only slightly increases the expression level of p21 as compared to the untreated control while single agent cisplatin treatment produced a dramatic increase in p21 mRNA expression. Combination studies, using concurrent treatment resulted in an increase in p21 mRNA level. However this increase was maintained at a reduced level compared with the appropriate cisplatin control. Sequential treatment resulted in a similar pattern; however the differences between single agent cisplatin treatment and sequential combination treatment were not as pronounced. Taken together, these data suggest that apoptosis and the lengthening of the cell-cycle may be primarily due to the increase in p21 mRNA expression level. Furthermore, the moderate differences in mRNA expression apparent with sequential treatment verses the concurrent control likely contribute to the synergy observed with sequential treatment. However, the slight decrease in p21 mRNA expression comparing single agent cisplatin and combination concurrent treatment does not correlate with the increase in the phosphorylation of p53 detected via western blot analysis. It is possible; however, that the increase in phosphorylated p53 may not translate directly into an increase in p21 expression or that this is require for p21 as p53 independent mechanisms may be involved, a possibility supported by results with H1299 p53 null cells. Further characterization of DNA repair proteins DDB2 and XPC demonstrate similar trends in mRNA expression levels as with p21. Taken together, the mRNA expression data is supportive of the synergistic and antagonistic results noted above for each treatment method. It also suggests that the inhibitors are altering not only the RPA-DNA binding activity but also the expression of other DNA repair proteins (XPC and DDB2) and tumor suppressor protein p21.

ATM, a protein kinase similar to ATR, initiates cell-cycle arrest in response to DNA double strand breaks (DSBs). ATM, which is recruited to the site of a DBS via the MRN complex (MRE11, Rad50 and NSB1) phosphorylates H2AX (γH2AX) and CHK2 resulting in cell cycle arrest and a lengthening of the S-phase of the cell cycle. Again, ATM phosphorylation increases moderately with cisplatin and combination MCI13E treatment in all cell lines analyzed and no detectable CHK2 or γH2AX signal was detected. Taken together, this data suggests that the cell cycle lengthening following single agent MCI or combination treatment is not due to an increase in ATM activation. Furthermore, combination treatment of A549 cell lines with MCI13E or F and ionizing radiation results in, at best, an additive increase in cell death (data not shown). This data, in addition to the ATM data, suggests that the SMIs do not elicit their cytotoxic effects by damaging both DNA strands resulting in a double strand break.

Although the data demonstrates an increase in cellular apoptosis and synergy between the SMIs and cisplatin, the direct interactions between the RPA protein and SMIs remains unclear. MCI13E is thought to react with cysteine residues, of which RPA contains 13. Four cysteine residues reside within the zinc-finger domain while the remaining residues are dispersed throughout the protein. Mutation analysis of each individual cysteine holds potential to reveal the direct interaction between the SMI and RPA. Moreover, demonstrating in vivo a direct SMI-RPA interaction would further confirm the specificity of the interaction already confirmed in vitro (10). Overall, these identified SMIs of RPA binding hold great potential for further characterizing the RPA-DNA interaction and delineating the specific role of individual RPA domains in DNA repair and replication. The synergy with chemotherapeutics like cisplatin suggest potential clinical benefits as well.

Materials and Methods

Phosphocellulose matrix was obtained from Sigma. Radiolabeled nucleotides were purchased from Perkin-Elmer Life Science (Boston, Mass.). All oligonucleotide substrates were purchased from Integrated DNA Technology (Coralville, Iowa) and gel purified by 12% polyacrylamide, 7M urea preparative denaturing gel electrophoresis. The 3Pc3 sequence is 5'-GGA GAC CGA AGA GGA AAA GAA GGA GAG AGG-3' (SEQ. ID No. 1), the 34-mer is 5'-CTA GAA AGG GGG AAG AAA GGG AAG AGG CCA GAG A-3' (SEQ. ID No. 2) and the 15-mer is 5'-GGT TAC GGT TAC CCC-3' (SEQ. ID No. 3).

Small Molecule Inhibitors of RPA.

All commercial reagents and solvents were reagent grade and used as received unless otherwise noted. $CH_2Cl_2$ was distilled from $CaH_2$ immediately prior to use. Celite® filtrations utilized Johns-Manville 545 material. Thin layer chromatography utilized silica gel plates (EM Science 5715) which were visualized with UV light, and stained with anisaldehyde. Boiling points were determined by Kugelrohr distillation using a Buchi GKR-50 apparatus. Reported values are oven temperature and are uncorrected. NMR spectra were obtained on a Bruker Avance II 400 MHz spectrometer. Chemical shifts are reported in ppm relative to TMS as calibrated by internal TMS or the residual protonated solvent signal. Coupling constants (J) are reported in Hz. Protons marked as 'a' or 'b' refer to the downfield and upfield protons respectively and do not represent stereochemistry. Carbon signals marked with an asterisk represent methyl and methine carbons, and quaternary carbons are designated with a (q) as determined by DEPT experiments. Quaternary resonances at C2 and C7 of the isoborneol skeleton were made on the basis of gHMBC spectra. Infrared spectra were recorded from films on a Thermo-Nicolet iS10 instrument using attenuated total reflectance (ATR) device.

CheSS19 was prepared as described (9). (+/−) isobornyl halo-esters (terpene derivatives) were prepared by the following general procedure. Briefly, to an ice-cooled solution of (+/−)-isoborneol (1.00 g, 6.48 mmol) in dry $CH_2Cl_2$ (25 mL) in a Schlenk tube under $N_2$ was added dicyclohexylcarbodiimide (1.60 g, 7.76 mmol), followed by the corresponding haloacid (7.15 mmol) and 4-dimethylaminopyridine (77 mg, 0.63 mmol). The clear colorless solution was stirred 18-24 hr at which time TLC analysis indicated complete consumption of isoborneol (Rf 0.26, 9:1 hexanes/EtOAc) and precipitates of dicyclohexylurea were evident. Diethyl ether (25 mL) was added, precipitating the bulk of the dicyclohexylurea. The mixture was filtered and the filter cake washed with ether (2×25 mL). The filtrate which had developed additional precipitate was refiltered and the solvent removed by rotary evaporation. Kugelrohr distillation of the residue afforded the halo-esters as colorless oils of greater than 90% purity. Additional experimental details concerning the synthesis and chemical characterization of these compounds can be found in U.S. Pat. No. 4,479,963 which is incorporated herein by reference in its entirety and in Murray, R. I.; Gunsalus, I. C.; Dus, K. M. Active Site Studies of Cytochrome P-450$_{CAM}$ I. Specific Cysteine Labeling with the Affinity Reagent Isobornyl Bromoacetate as a Model for Substrate Binding. *J. Biol. Chem.* 1982, 257, 12517-12525.

Figure 9A:
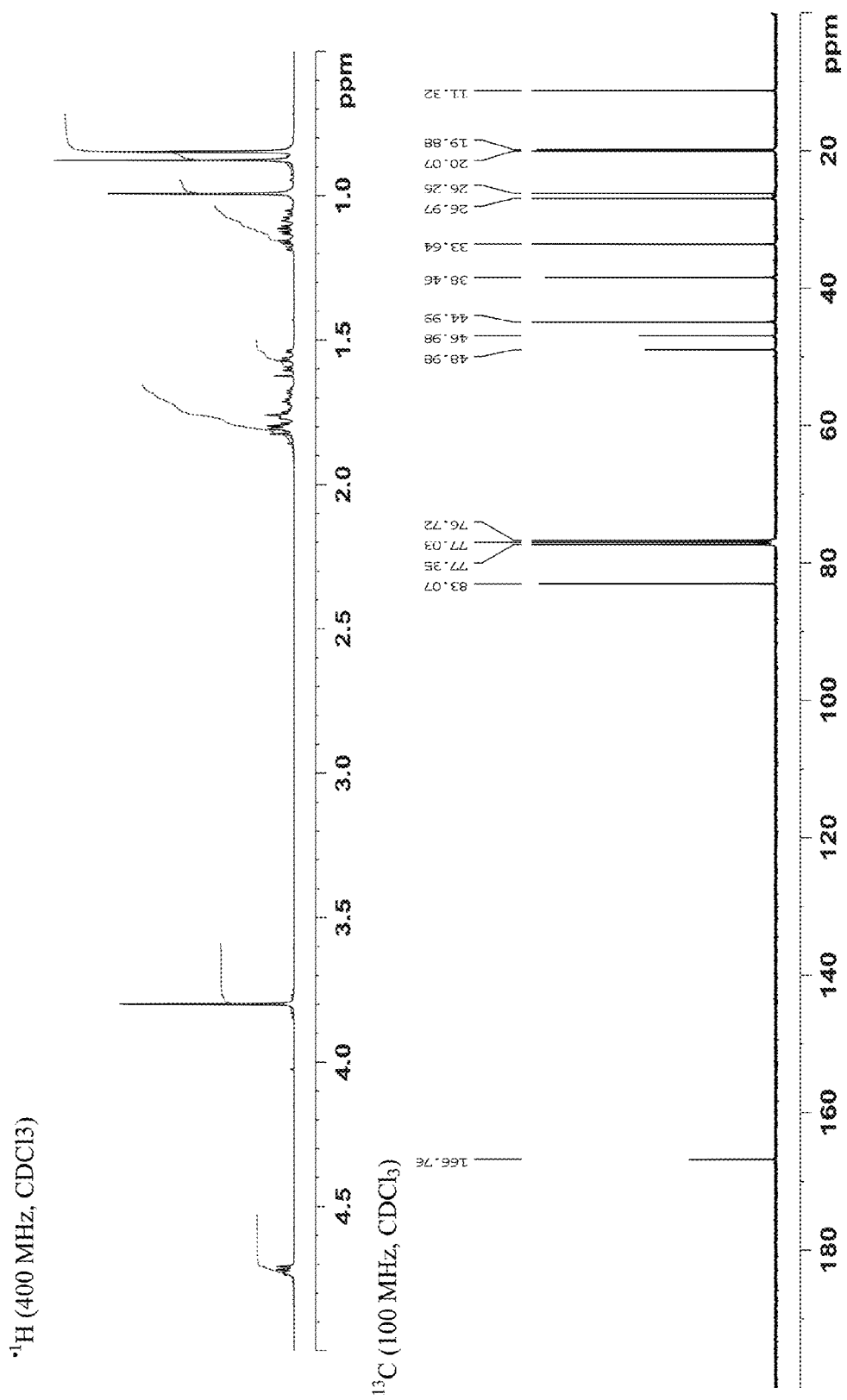
FIG. 9A. Structure of MCI13E determined by $^1$H and $^{13}$C NMR.
Figure 9B:
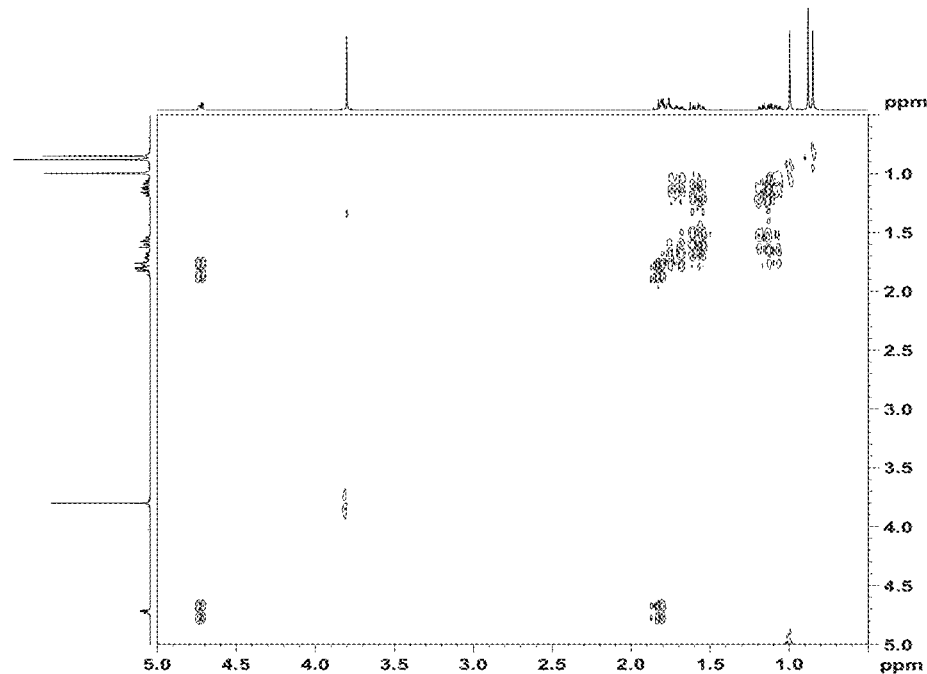
FIG. 9B. Structure of MCI13E determined by gdqCOSY and gHSQC (DEOT edited).
Figure 9B:
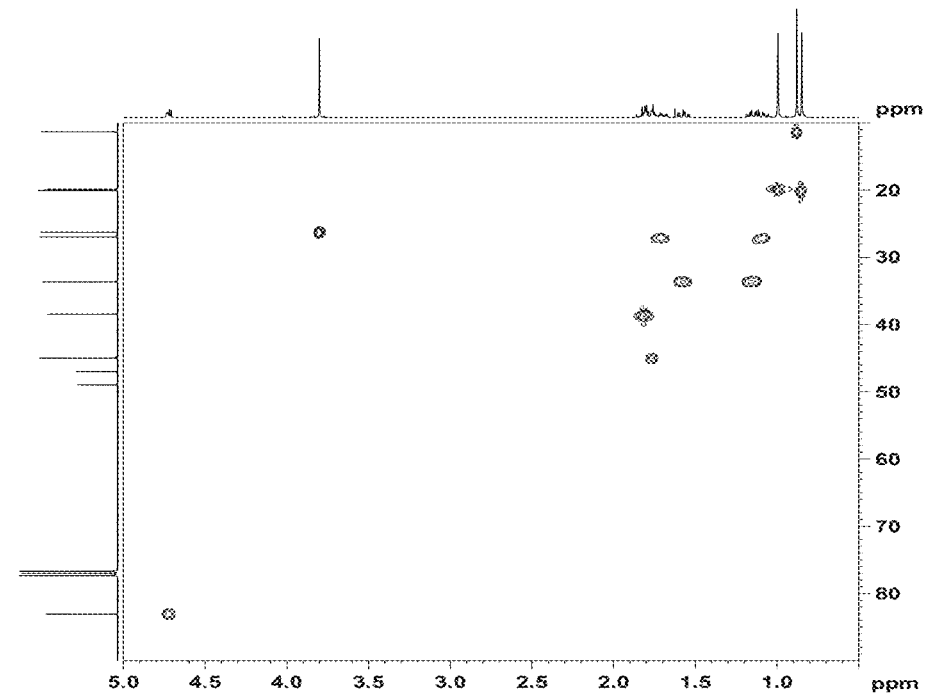
Figure 10A:
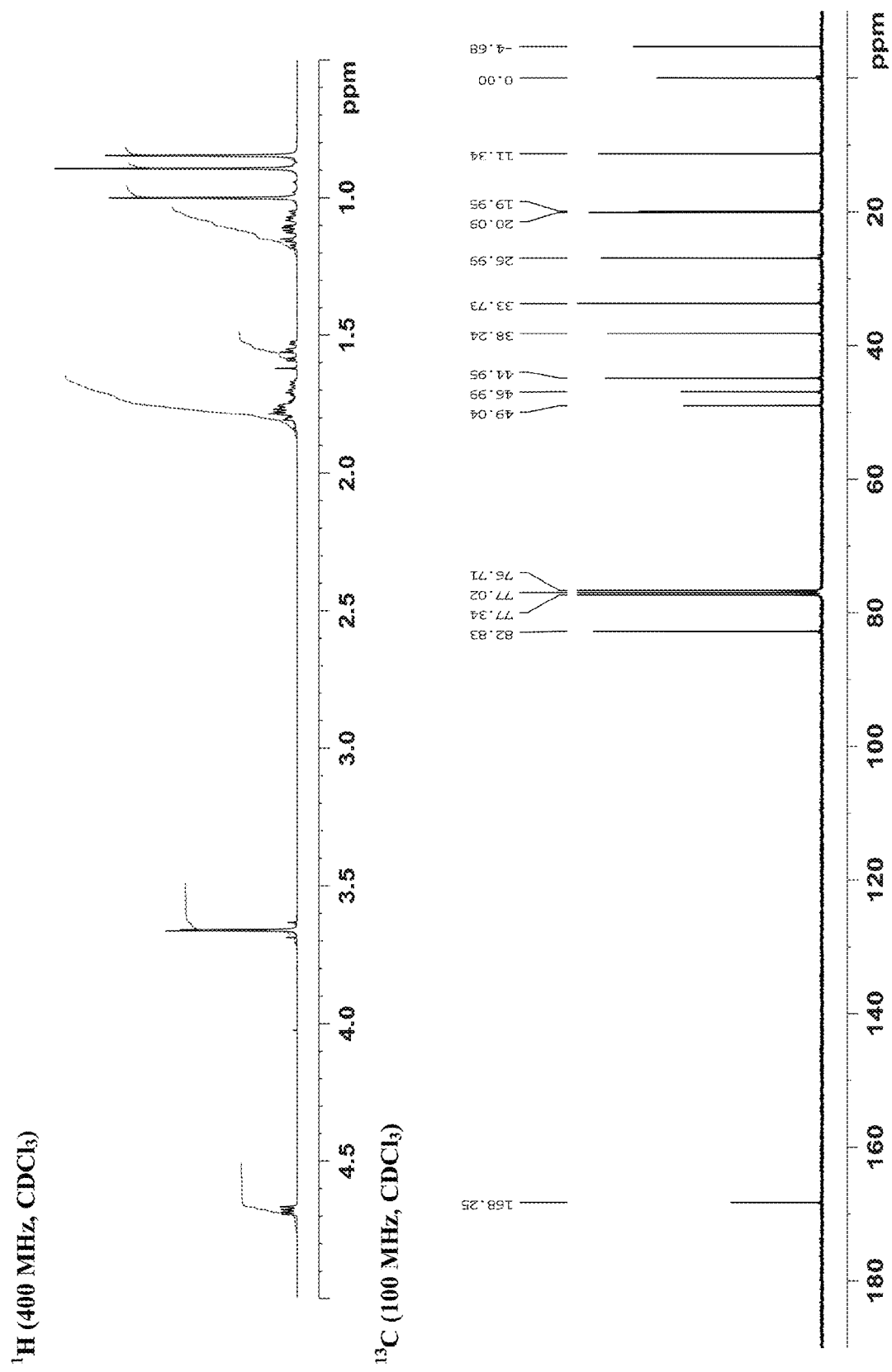
FIG. 10A. Structure of MCI13F determined by $^1$H and $^{13}$C NMR.
Figure 10B:
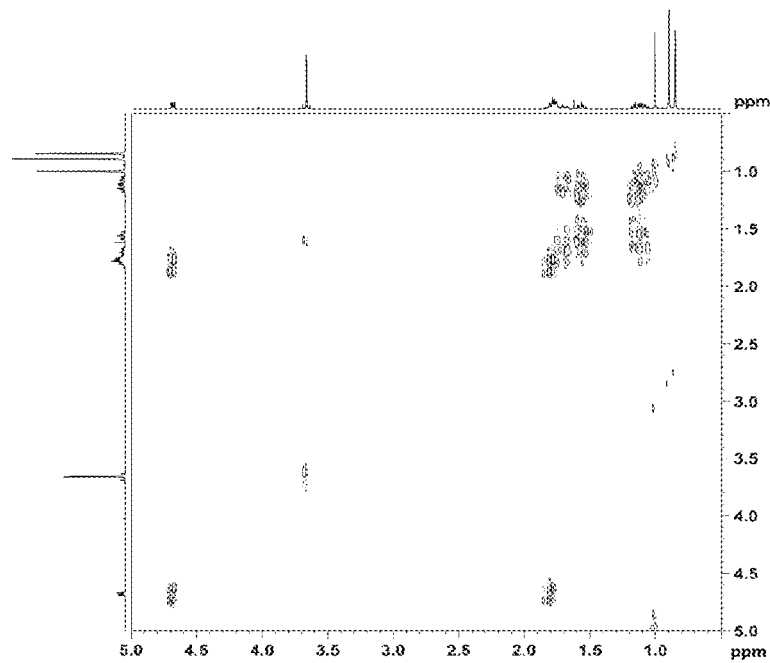
FIG. 10B. Structure of MCI13F determined by gdqCOSY and gHSQC (DEPT edited).
Figure 10B:
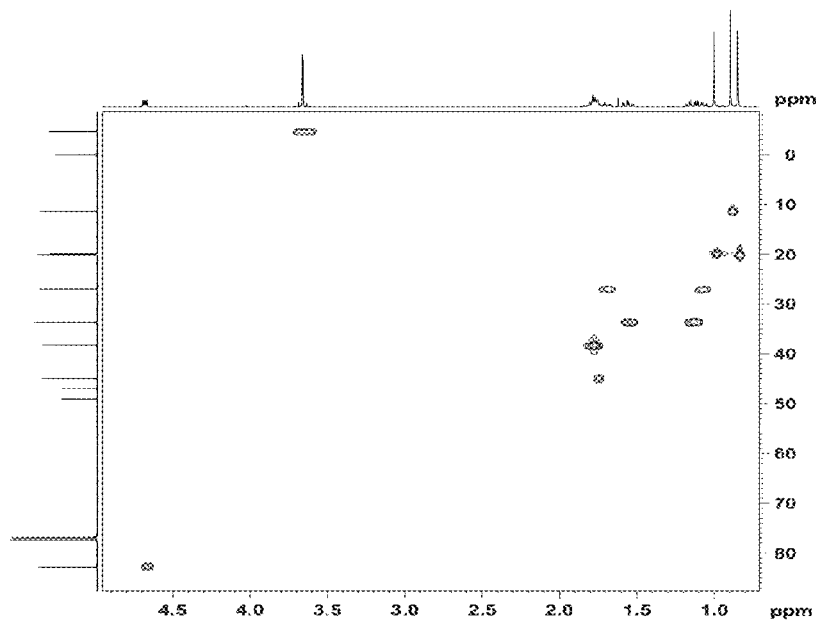

The structures and NMR assignments are illustrated in FIGS. 9 and 10. (+/−)-Isobornyl bromoacetate (1) Yield 1.54 g (87%); B.p. 70-80° C. (0.03 mmHg); TLC Rf 0.57 (9:1 hexanes/EtOAc); $^1$H NMR (400 MHz,) δ 4.72 (m, 1H, H1), 3.80 (s, 2H, H12), 1.81 (m, 2H, H6), 1.77 (m, 1H, H5), 1.71 (m, 1H, H4a), 1.57 (td, J=4.1, 12.5, 1H, H3a), 1.16 (m, 1H, H3b), 1.09 (m, 1H, H4b), 0.99 (s, 3H, H8), 0.88 (s, 3H, H10), 0.85 (s, 3H, H9); $^{13}$C NMR (100 MHz,) δ 166.76q (C11), 83.07* (C1), 48.98q (C7), 46.98q (C2), 44.99* (C5), 38.46 (C6), 33.63 (C3), 26.97 (C4), 26.26 (C12), 20.07* (C9), 19.88* (C8), 11.32* (C10); IR ($v_{max}$, cm$^{-1}$) 2954, 2876, 1728, 1455, 1391, 1279, 1164, 1109, 1049, 1005, 982, 838.

(+/−)-Isobornyl iodoacetate: (2) Yield 1.85 g (88%); B.p. 80-90° C. (0.03 mmHg); TLC Rf 0.61 (9:1 hexanes/EtOAc); $^1$H NMR (400 MHz,) δ 4.72 (dd, J=3.5, 7.1, 1H, H1), 3.66 (d, J=1.7, 2H, H12), 1.77 (m, 2H, H6), 1.75 (m, 1H, H5), 1.69 (m, 1H, H4a), 1.55 (td, J=4.0, 12.6, 1H, H3a), 1.14 (m, 1H, H3b), 1.07 (m, 1H, H4b), 1.00 (s, 3H, H8), 0.90 (s, 3H, H10), 0.85 (s, 3H, H9); $^{13}$C NMR (100 MHz,) δ 168.25q (C11), 82.83* (C1), 49.04q (C7), 46.99q (C2), 44.95* (C5), 38.24 (C6), 33.73 (C3), 26.99 (C4), 20.09* (C9), 19.95* (C8), 11.34* (C10), −4.68 (C12); IR ($v_{max}$, cm$^{-1}$) 2951, 2876, 1545, 1391, 1262, 1083, 1049, 1004, 982, 823.

Protein Expression and Purification.

RPA. Human full-length, un-tagged heterotrimeric RPA (RPA) was purified as previously describe [17].

DBD-A/B. The sequence encoding the RPA p70 DNA binding domains A and B were subcloned from the hrRPA plasmid (provided by Dr. Marc Wold, University of Iowa) into the pET15b (Novagen) vector and the protein was expressed in BL21(DE3) cells (Stratagene) as previously described. Briefly, cells were grown to an OD$_{600}$ of 0.8, induced with 0.5 mM isopropyl-1-thio-β-D-galactopyranoside (IPTG) at 37° C. for 2-3 hours. Small scale DBD-A/B preparations were obtained from 1 L cultures and following induction, cells were harvested by centrifugation at 700×g for 30 minutes at 4° C. The pellets were suspended in Buffer A (20 mM Tris, pH 7.5, 10% glycerol, 500 mM NaCl, 10 mM β-mercaptoethanol (BME) and 1 µg/mL phenylmethanesulfonylfluoride (PMSF), leupeptin and pepstatin) at 1 mL/gram of cells. The cells were lysed by sonication and insoluble material sedimented at 15,000×g for 30 minutes at 4° C. The supernatant was then loaded onto a 10 mL phosphocellulose column, equilibrated with Buffer A, and the flow-through material collected. Imidazole was added to 5 mM to the flow through which was then loaded onto a 2 mL nickel-NTA-agarose column. The column was then washed with Buffer A containing 50 mM imidazole after which protein was eluted from the column using a gradient from 50-500 mM imidazole. Fractions were analyzed for protein content using Bradford and SDS-PAGE analysis in addition to assessment of DNA binding activity as determined by anisotropy. Fractions containing the DBD-A/B protein were pooled and dialyzed overnight in Buffer B (1 mM HEPES, pH 7.2, 10 mM dithiothreitol (DTT), 50 mM NaCl and 1 µg/mL PMSF, pepstatin and leupeptin) and aliquots stored at −80° C.

Fluorescence Polarization Assays.

Fluorescence polarization experiments were preformed as previously described (21). Reactions contained 20 nM F-dT$_{12}$ and the concentrations of RPA and DBD-A/B indicated in the figure legends. SMIs were diluted in H1 buffer (10 mM HEPES, pH 7.2, 1 mM DTT, 0.01% NP-40 and 100 mM NaCl) and the final DMSO concentration was kept below 1%.

Electrophoretic Mobility Shift Assay (EMSA).

RPA and DBD-A/B Binding. EMSAs were performed as previously described (22) using a 30-base purine rich ssDNA substrate (3Pc3). Briefly, reactions contained 12.5 nM 5'-[$^{32}$P]-labeled 3Pc3 ssDNA and the indicated concentrations of RPA or DBD-A/B. Protein was pre-incubated with the indicated concentration of SMI for 30 minutes at 37° C. DNA was then added and reactions incubated for an additional 5 minutes at room temperature in a final reaction volume of 40 µL. Reactions were then resolved on a 6% native polyacrylamide gel and electrophoresed at 170 volts for 1 hour. Gels were dried and quantified via phosphorimager analysis and ImageQuant software (Molecular Dynamics).

E. coli SSB Binding Assays.

EMSAs were performed similarly to those for the RPA constructs, with the following exceptions. Reactions contained 25 nM of 5'-[$^{32}$P]-labeled 3Pc3 ssDNA and 3.3 nM (assuming homotetramer formation) SSB protein (Enzymatics, Beverly, Mass.). Reactions (20 µL) were carried out in 20 mM HEPES, pH 7.5, 1 mM DTT, 0.01% NP-40, 100 mM NaCl, and resolved by 6% native polyacrylamide gel electrophoresis at 25 mA for 2 hours. Gels were dried and quantified via phosphorimager analysis and ImageQuant software (Molecular Dynamics).

Analysis of Reversible Inhibition.

In order to assess the reversibility of select SMIs, the indicated SMI was pre-incubated with RPA or the DBD-A/B construct for 30 minutes at room temperature. The resulting solution was dialyzed versus 500 mL H1 buffer at 4° C. using 0.5 ml, 12,000 molecular weight cut-off dialysis cassettes (Pierce). The resulting protein was recovered and concentration determined by Bradford analysis. Analysis of DNA binding activity was performed either by EMSA or FP. In each series of experiments, there was no loss of DNA binding activity in vehicle control treated protein.

Chemicals—Dulbecco's Modified Eagle Media (DMEM), RPMI, fetal bovine serum (FBS), penicillin/streptomycin and trypsin were purchased from CellGro (Manassas, Va.). Annexin V-FITC/propidium idodine (PI) Vybrant Apoptosis Assay kit and the GAPDH primary antibody were purchased from Invitrogen (Carlsbad, Calif.). Dimethyl sulfoxide (DMSO) and sodium dodecyl sulfate (SDS) was purchased from Fisher Scientific (Pittsburgh, Pa.). Cell Counting Kit-8 solution was purchased from Dojindo Laboratories (Rockville, Md.) and primary antibodies against p53 and ATM were supplied by Abcam (Cambridge, Md.). Secondary antibodies were purchased from Bio-Rad (Hercules, Calif.) and Santa Cruz (Santa Cruz, Calif.). All other reagents and chemicals were purchased from Sigma Aldrich (Milwaukee, Wis.) or Fisher Scientific (Houston, Tex.).

Cell lines—Tumor cell lines A549 (lung, CCL-185), H1299 (p53-deficient lung, CRL-5803), and H460 (HTB-177) were obtained from the American Type Culture Collection, verified via STR testing (Manassas, Va.) and were not passaged over 6 months following resuscitation. The A2780 line was obtained from Tom Hamilton at FCCC. The A549, H1299 and A2780 cells were maintained in Dulbecco's modified Eagle medium supplemented with 1% penicillin/streptomycin and 10% fetal bovine serum. H460 cells were maintained in RPMI media containing 1% penicillin/streptomycin and 10% FBS. Cells were maintained in a humidified incubator at 37° C. with 5% CO2 supplementation.

Cell Viability Assays—A crystal violet cell viability assay was performed to determine cytotoxicity of SMI. Lung cancer cell lines, A549 and H460, were plated in 24-well dishes at 5×10$^4$ total cells. Forty-eight hours after plating, the cells were treated for 24 hours with variable concentrations of SMIs. The media was aspirated, cells washed with 500 µl of PBS/EDTA and stained for 10 minutes with crystal violet solution (50% Ethanol, 0.75% crystal violet). Stained cells were resuspended in 500 µl DMSO containing 1% SDS and absorbance was measured at 590 nm in a SpectraMax M5 plate reader (Molecular Devices, Sunnyvale, Calif.) and analyzed using SoftMax Pro 5.2. Percent viability is taken as an absorbance percentage against control untreated cells. Values plotted represent four separate plate replicates and each plate replicate contained three assay replicates per plate.

Ovarian cancer cell line, A2780, cells are difficult to use for crystal violet analysis due to their enhanced sensitivity to treatment. Therefore, the cell counting kit-8 (CCK) was used to determine the viability of A2780 cells in addition to the p53 null lung cancer cell line H1299, following a 24 hour treatment with log dosing of SMI. Cells were plated ($1 \times 10^5$) in 24-well dishes and treated with inhibitor after 24 hours. After treatment media was aspirated and 1 ml of DMEM was added in addition to 100 µL of CCK-8 solution. Absorbance at 450 nm was measured over 4 hours in a SpectraMax M5 plate reader and values are presented as the percent untreated control at the two hour time point for three separate plate replicates each containing three assays per plate.

Flow Cytometry—After determining the SMI cytotoxicity, H460, A549 and H1299 lung cancer cell lines were analyzed for apoptosis using the Annexin V-FITC/Propidium Iodide (PI) Vybrant® Apoptosis Assay kit (Invitrogen, Gaithersburg, Md.). Cells were plated in 6-well dishes ($2 \times 10^5$ cells total), treated for 24 (H1299) or 48 (H460 and A549) hours with increasing concentrations of SMI. Following treatment, both adherent and non-adherent cells were collected, processed via the manufacturer's protocol (Invitrogen) and analyzed on a FACScan flow cytometer (Becton Dickson, San Jose, Calif.). Data was analyzed using WinDMI software (The Scripps Research Institute, Can Diego, Calif.) and results are presented as a percentage of control (untreated cells).

Cell cycle analysis was also performed on the three lung cancer cell lines using PI staining to identify the potential arrest resulting from treatment with SMIs. Briefly, cells were plated in 6-well dishes ($2 \times 10^5$ cells total) and treated for 6 or 12 hours with increasing concentration of inhibitor. Adherent and non-adherent cells were collected, washed twice with PBS containing 2% bovine serum albumin (BSA), resuspended in 70% cold EtOH and incubated overnight at $-20°$ C. Cells were again collected and stained with PI (1 µg/mL) and RNaseA (25 µg/mL) for 30 min. at 37° C. followed by 1.5 hours at 4° C. in the dark. Flow cytometry was performed as above and data were analyzed on a histogram with events plotted against the FL2-A parameter. Cell cycle distribution was analyzed using the ModFit software and data presented represents three independent trials.

A549 cells were also treated sequentially or concurrently with combination treatment utilizing cisplatin and SMIs. Sequentially treated cells were plated ($3 \times 10^5$ total cells) in 6-well dishes and treated 12 hours later with cisplatin (5 µM) for 12 hours at which time SMIs (7 µM) were added as indicated. Cells were then processed (as described above for cell cycle analysis) at 6 and 12 and 24 hours after the addition of SMI. Concurrently treated cells were plated in E-well dishes, media was changed 12 hours after initial plating and cells were treated with cisplatin (5 µM) and SMIs (7 µM) after an additional 12 hours. Cells were then processed at 6, 12, and 24 hours post combination treatment for PI staining as described above.

Figure 17A:
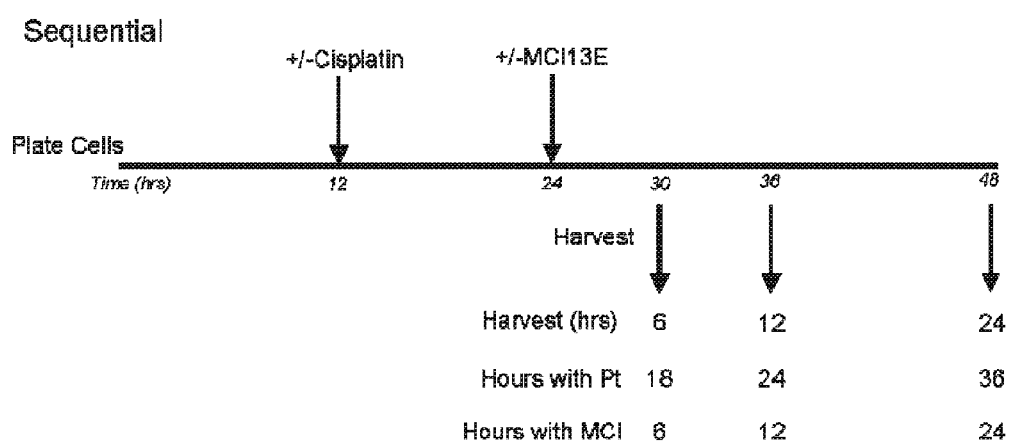
FIG. 17A. Schematic of sequential treatment regime.
Figure 17B:
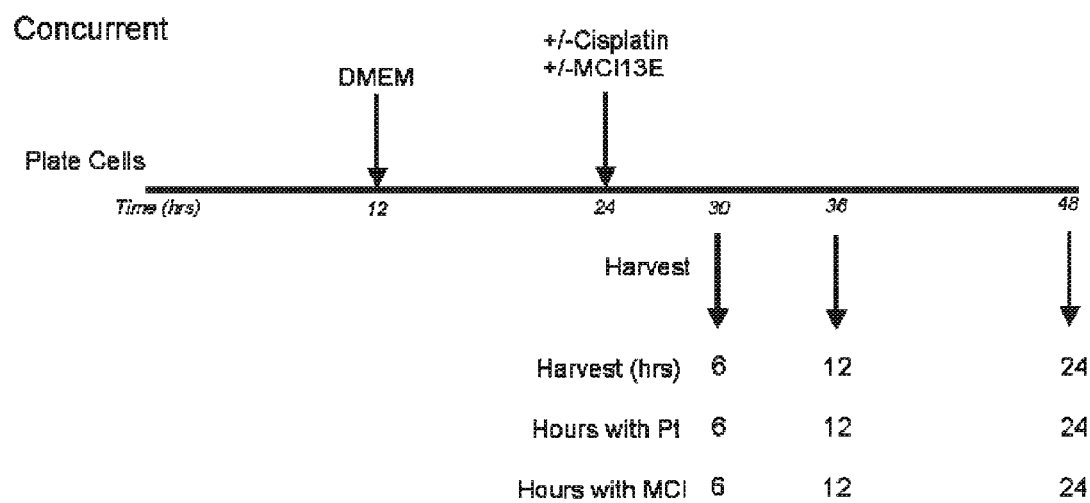
FIG. 17B. Schematic of concurrent treatment regime.

In order to keep the cisplatin treatment constant and monitor cell cycle progression, a similar methodology was applied. Twelve hours after initial plating, A549 cells were treated with cisplatin (2.5 µM). Following either 12 or 24 hours of cisplatin treatment, MCI13E was added to the media (5 µM) and cells were processed 12 or 24 hours later and analyzed for PI incorporation as discussed above (see FIGS. 17A and 17B).

Combination Index—Studies Combination index studies, performed with combination SMI and cisplatin treatment, were used to determine the level of synergy or antagonism between the two compounds. Referring now to FIG. 19A, a schematic illustrating Sequential treatment with cisplatin and MCI13E, and FIG. 19B, a schematic illustrating concurrent treatment with cisplatin and MCI13E. Cells received the same concentration of cisplatin or MCI13E but the time the cells were treated with cisplatin varied whereas treatment time with MCI remained the same between the two treatment methods.

Briefly, A549 cells were plated as described above in 24-well dishes ($5 \times 10^4$ cells per well) and treated either concurrently or sequentially with single agent cisplatin or MCI treatment or with combination treatments. For sequential treatment, A549 cells were treated with cisplatin (0, 0.9, 1.8, 3.7, or 15 µM) for 24 hours and then the inhibitor was added to the media for an additional 24 hours (0, 0.75, 1.5, 3, 6 or 12 µM for E and 0, 0.25, 0.5, 1, 2, 4 µM for F). Concurrently treated cells were treated with both cisplatin and inhibitor for a full 48 hours. Following 48 hours of total treatment cells were analyzed for viability using the crystal violet assay described above and combination index values were calculated based on the Chou and Talalay method (15) as we have previously described (1,23).

Figure 16B:
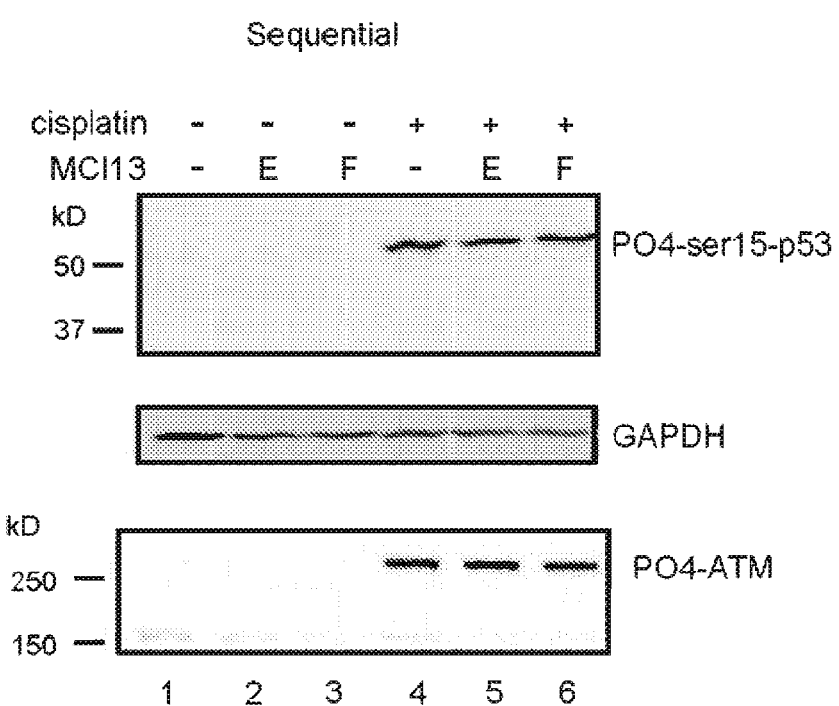
FIG. 16B. Western blot analysis of cells following sequential treatment regime.

Real-Time PCR—A549 cells were plated in 10 cm dishes at $1.5 \times 10^6$, allowed to adhere, and treated for 24-48 hours with cisplatin or SMIs (5 µM). Referring now to FIG. 16B, Western blot of cells treated sequentially. For sequential treatment, A549 cells were exposed to cisplatin for 24 hours followed by the addition of SMIs for another 24 hours as above. Referring now to FIG. 16A, A549 cells were treated sequentially or concurrently with cisplatin (5 µM) and MCI13E or MCI13F for 24 total hours. Lysates were probed for p53-ser15-phosphorylation or phosphorylated-ATM. GAPDH was probed as a loading control. Concurrently treated cells were incubated simultaneously with both cisplatin and MCIs for 24 hours. RNA was extracted using RNeasy minikit (Qiagen, Germantown, Md.) per manufacturer's protocol. cDNA was generated using Applied Biosystem's (ABI) High Capacity RNA-to-cDNA kit. Validated gene primer/probe sets, also from ABI, were used for Quantitative Real Time-PCR. ABI's ΔΔCT Relative Quantification methodology was used for the analyses (applied Biosystems). Data were normalized to the housekeeping gene GAPDH and calibrated to the mock treated samples. Results presented are the average of two separate cell treatments/RNA isolations with duplicate Taqman Assays per RNA sample set.

Figure 15A:
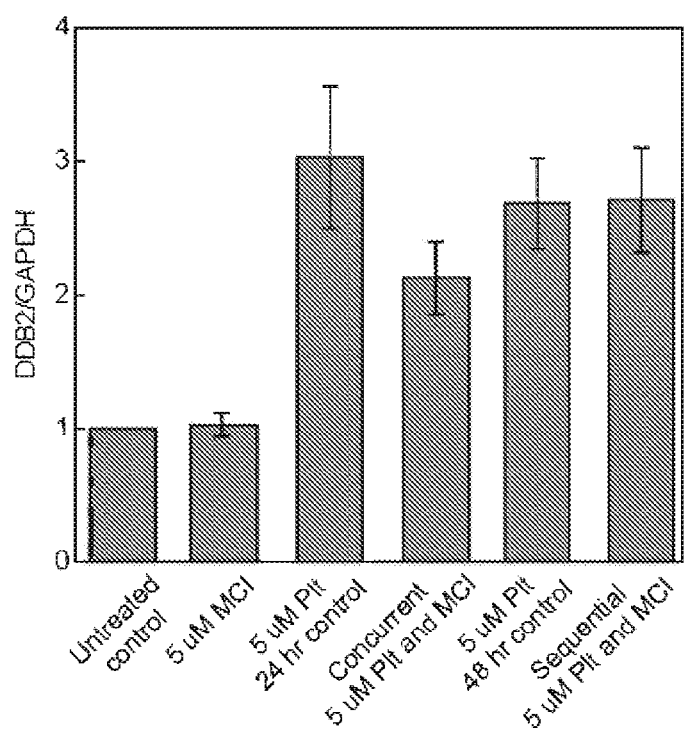
FIG. 15A. Plot of Quantitative Real Time PCR analyses of mRNA expression changes of A549 cells treated with MCI13E, MCI13F and Cisplatin.
Figure 15B:
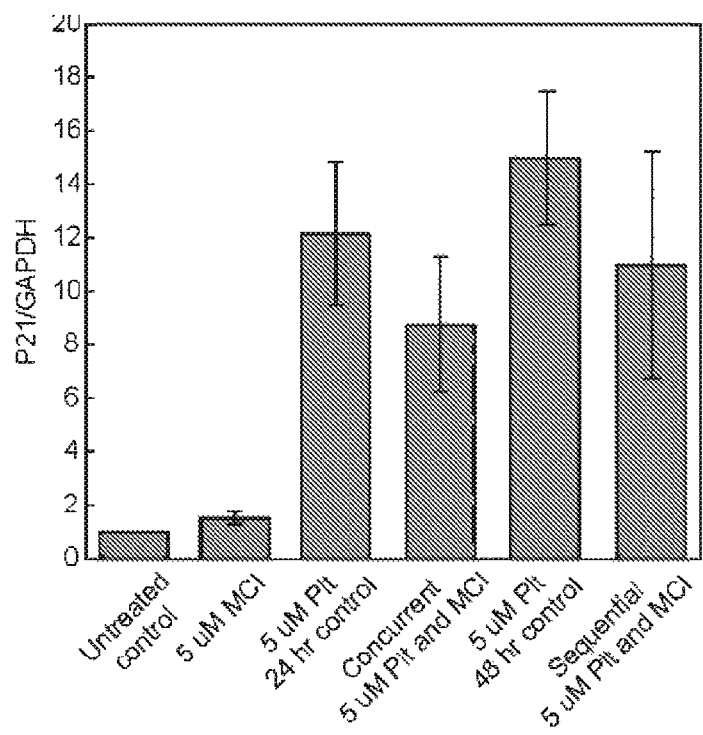
FIG. 15B. Bar graph of P21/GAPDH measured in cells subjected to different treatment schemes.
Figure 15C:
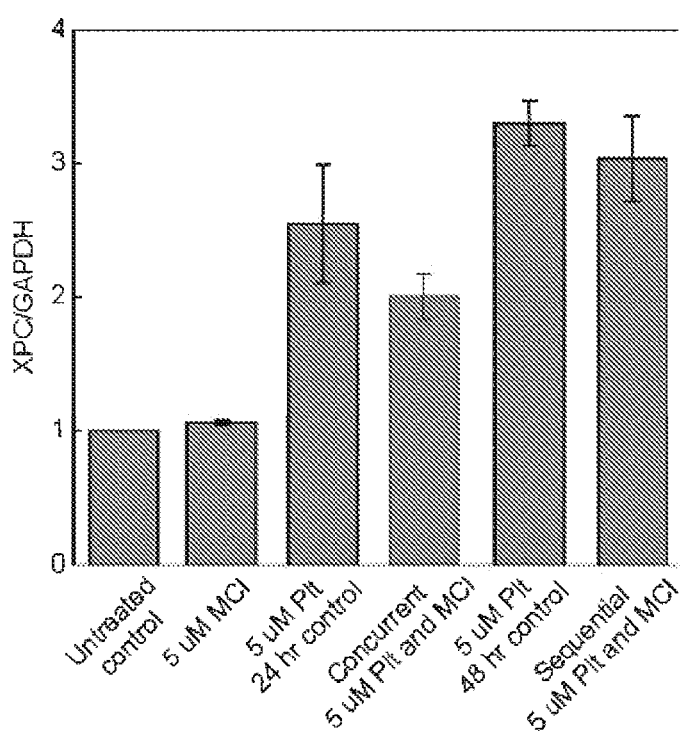
FIG. 15C. Bar graph of XPC/GAPDH measured under different treatment regimes XPC.

Referring now to FIG. 15A. Plot of Quantitative Real Time PCR analyses of mRNA expression changes of A549 cells treated with MCI13E, MCI13F and Cisplatin. Data represents the average of four separate Q-RT PCR Assays. Genes of interest were normalized to GAPDH transcript levels, and are presented as fold changes relative to untreated cell samples. Cisplatin treatment increases transcription of DDB2 (A). Referring now to FIG. 15B. Bar graph of P21/GAPDH measured in cells subjected to different treatment schemes. Referring now to FIG. 15C. Bar graph of XPC/GAPDH measured under different treatment regimes XPC Concurrent MCI/Cisplatin treated cells show a decrease in gene transcription when compared to cells treated with Cisplatin alone (24 hour).

Western Blot Analysis—Cells lines (A549, H460, or H1299) were plated in 10 cm dishes ($3 \times 10^6$) and treated with the ~$IC_{50}$ concentration of SMIs in the absence or presence of cisplatin (5 µM for A549 and H460 and 10 µM for H1299 cells). Twenty-four hours following treatment the media was aspirated and adherent cells were washed with 5 mL of PBS/EDTA. Adherent cells were scraped from the plates into 100 µL of RIPA buffer (10 mM Tris, pH 7.2, 150 mM NaCl, 0.1% SDS, 1% Triton X-100, 1% Deoxycholate, 5 mM EDTA) and cellular debris was pelleted by centrifugation (10,000×g, 10 min., 4C). The supernatant was collected into a 1.5 mL microfuge tube and total protein concentration was determined (Bio-Rad, Hercules, Calif.) standardized against BSA. Equal amounts of protein (40 μg) were loaded onto SDS-PAGE and following electrophoresis proteins were transferred to polyvinylidene difluoride membranes. Proteins were detected with various antibodies (1:2000 dilutions) and goat anti-mouse or goat anti-rabbit horseradish peroxidase secondary antibodies (1:2500 or 1:3000), respectively. Chemiluminescence and an Image Reader LAS3000 (Fujifilm) were employed to visualize bands while Multi Gauge V3.0 software was used for data analysis.

REFERENCES

1. Shuck, S. C. and Turchi, J. J. (2010) *Cancer Res.* 70, 3189-3198
2. Bochkarev, A., Pfuetzner, R. A., Edwards, A. M., and Frappier, L. (1997) *Nature* 385, 176-181
3. Lei, M., Podell, E. R., and Cech, T. R. (2004) *Nat. Struct. Mol. Biol.* 11, 1223-1229
4. Wold, M. S. (1997) *Annual Review of Biochemistry* 66, 61-92
5. Bochkarev, A. and Bochkareva, E. (2004) *Current Opinion in Structural Biology* 14, 36-42
6. Theobald, D. L., Mitton-Fry, R. M., and Wuttke, D. S. (2003) *Annu. Rev. Biophys. Biomol. Struct.* 32, 115-133
7. Bochkareva, E., Korolev, S., Lees-Miller, S. P., and Bochkarev, A. (2002) *EMBO J.* 21, 1855-1863
8. Andrews, B. J. and Turchi, J. J. (2004) *Mol Cancer Ther* 3, 385-391
9. Turchi, J. J., Shuck, S. C., Short, E. A., and Andrews, B. J. (2009) Targeting Nucleotide Excision Repair as a Mechanism to Increase Cisplatin Efficacy. In Bonetti, A., Leone, R., Muggia, F. M., and Howell, S. B., editors. *Platinum and Other Heavy Metal Compounds in Cancer Chemotherapy*, Humana Press, New York
10. Anciano Granadillo, V. J., Earley, J. N., Shuck, S. C., Georgiadis, M. M., Fitch, R. W., and Turchi, J. J. (2010) *J. Nucleic Acids* 2010, 304035
11. Lei, M., Podell, E. R., Baumann, P., and Cech, T. R. (2003) *Nature* 426, 198-203
12. Raghunathan, S., Kozlov, A. G., Lohman, T. M., and Waksman, G. (2000) *Nat. Struct. Biol.* 7, 648-652
13. Einhom, L. H. (2002) Proceedings of the National Academy of Sciences of the United States of America 99, 4592-4595
14. Neher, T. M., Bodenmiller, D. A., Fitch, R. W., Jalal, S., and Turchi, J. J. (2011) Novel Irreversible Small Molecule Inhibitors of Replication Protein A Display Single Agent Activity and Synergize with Cisplatin.
15. Chou, T. C., Talalay, P., and (1984) *Advances in Enzyme Regulation* 22, 27-55
16. Haring, S. J., Mason, A. C., Binz, S. K., and Wold, M. S. (2008) *J. Biol. Chem.* 283, 19095-19111
17. Wakasugi, M. and Sancar, A. (1999) *J. Biol. Chem.* 274, 18759-18768
18. Wood, R. D. (1997) *J. Biol. Chem.* 272, 23465-23468
19. Cimprich, K. A. and Cortez, D. (2008) *Nat. Rev. Mol. Cell Biol.* 9, 616-627
20. Zou, L. and Elledge, S. J. (2003) *Science* 300, 1542-1548
21. Andrews, B. J., Lehman, J. A., and Turchi, J. J. (2006) *J. Biol. Chem.* 281, 13596-13603
22. Patrick, S. M. and Turchi, J. J. (2002) *J. Biol. Chem.* 277, 16096-16101
23. Boeckman, H. J., Trego, K. S., and Turchi, J. J. (2005) *Mol. Cancer Res.* 3, 277-285

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method of treating cancer, comprising:
(a) treating a patient with a therapeutically effective amount of a halo-ester isoborneol compound selected from the group consisting of

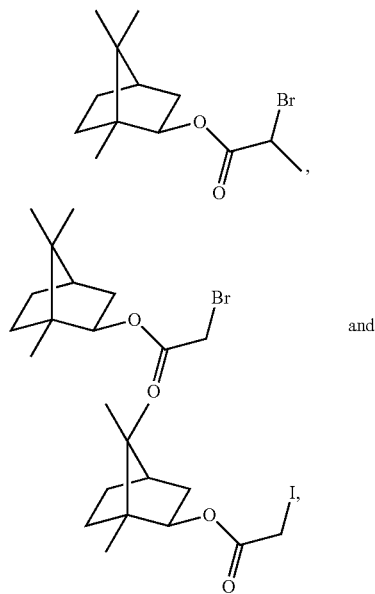

or a pharmaceutically acceptable salt thereof, wherein said halo-ester isoborneol compound at least partially inhibits the activity of Replication Protein A in vivo, wherein the cancer is non-small cell lung cancer or ovarian cancer.

2. The method according to claim 1, further comprising the step of:
(b) treating the patient with a therapeutically effective amount of at least one compound that damages DNA in vivo.

3. The method according to claim 2, wherein the compound that damages DNA in vivo promotes the formation of intra strand linkages between adjacent nucleotides.

4. The method according to claim 3, wherein the compound that damages DNA is cisplatin, or a pharmaceutically acceptable salt thereof.

5. The method according to claim 2, wherein the step of treating the patient with the compound that damages DNA occurs before the step of treating the patient with the halo-ester isoborneol compound.

6. The method according to claim 1, wherein the therapeutically effective amount is between about 100 mg/kg of patient body weight and about 300 mg/kg of patient body weight.

7. The method according to claim 6, wherein the therapeutically effective amount is about 200 mg/kg of patient body weight.

8. The method according to claim 1, wherein said therapeutically effective amount is less than about 400 mg of pharmaceutically active compound per kg of patient body weight.

9. The method according to claim 8, wherein said therapeutically effective amount is between about 50 mg to about 10 mg of pharmaceutically active compound per kg of patient body weight.

* * * * *

SEQUENCE LISTING

```
<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Synthetic oligonucleotide substrate of the 3Pc3
      sequence

<400> SEQUENCE: 1
ggagaccgaa gaggaaaaga aggagagagg                                            30

<210> SEQ ID NO 2
<211> LENGTH: 34
<212> TYPE: DNA
<213> ORGANISM: Artificial Sequence
<220> FEATURE:
<223> OTHER INFORMATION: A 34-mer synthetic oligonucleotide substrate

<400> SEQUENCE: 2
ctagaaaggg ggaagaaagg gaagaggcca gaga                                       34
```

```
<210> SEQ ID NO 3
<211> LENGTH: 15
<212> TYPE: DNA
<213> ORGANISM: Artificial Sequence
<220> FEATURE:
<223> OTHER INFORMATION: A 15-mer synthetic oligonucleotide substrate

<400> SEQUENCE: 3
ggttacggtt acccc                                                    15
```